(12) United States Patent
Kiss

(10) Patent No.: US 7,374,754 B2
(45) Date of Patent: *May 20, 2008

(54) USE OF PLACENTAL ALKALINE PHOSPHATASE TO PROMOTE SKIN CELL PROLIFERATION

(75) Inventor: Zoltan Kiss, Austin, MN (US)

(73) Assignee: Essential SkinCare, LLC, Austin, MN (US)

( * ) Notice: Subject to any disclaimer, the term of this patent is extended or adjusted under 35 U.S.C. 154(b) by 626 days.

This patent is subject to a terminal disclaimer.

(21) Appl. No.: 10/653,622

(22) Filed: Sep. 2, 2003

(65) Prior Publication Data

US 2005/0048046 A1 Mar. 3, 2005

(51) Int. Cl.
*A61K 38/43* (2006.01)
*A61K 31/74* (2006.01)

(52) U.S. Cl. .................................. 424/94.1; 424/78.02

(58) Field of Classification Search ..................... None
See application file for complete search history.

(56) References Cited

U.S. PATENT DOCUMENTS

| | | | |
|---|---|---|---|
| 4,030,995 A | 6/1977 | Starkweather | |
| 4,265,233 A | 5/1981 | Sugitachi et al. | |
| 4,556,056 A | 12/1985 | Fischer et al. | |
| 4,818,540 A | 4/1989 | Chien et al. | |
| 5,179,086 A * | 1/1993 | Flender | 514/182 |
| 5,487,889 A | 1/1996 | Eckert et al. | |
| 5,707,624 A | 1/1998 | Nickoloff et al. | |
| 6,265,436 B1 | 7/2001 | Appere et al. | |
| 6,290,952 B1 | 9/2001 | Poelstra et al. | |
| 6,414,036 B1 * | 7/2002 | Ninkov | 514/731 |
| 2002/0127216 A1 | 9/2002 | Kiss | |

FOREIGN PATENT DOCUMENTS

| | | |
|---|---|---|
| DE | 3007226 | 9/1981 |
| JP | 61-277626 | 12/1986 |
| SU | 1138410 | 2/1985 |
| SU | 1814764 | 3/1995 |
| WO | WO 92/14480 | 9/1992 |

OTHER PUBLICATIONS

Computer generated Babel Fish Translation of the Description of Patent DE 3007226 (2 pages).
Begoun, "Don't Go to the Cosmetics Counter Without Me. An Eye-Opening Guide To Brand-Name Cosmetics", 3$^{rd}$ Edition, Beginning Press © 1996.
Winter, "A Consumer's Dictionary of Cosmetic Ingredients", 4$^{th}$ Edition, Three Rivers Press © 1978.
Millan et al., "Biology of Human Alkaline Phosphatases with Special Reference to Cancer", *Critical Reviews in Clinical Laboratory Sciences*, 32(1):1-39 (1995).
She et al., "Growth Factor-Like Effects of Placental Alkaline Phosphatase in Human Fetus and Mouse Embryo Fibroblasts", *FEBS Letters* 469 (2000) 163-167.
She et al., "Placental Alkaline Phosphatase, Insulin, and Adenine Nucleotides or Adenosine Synergistically Promote Long-Term Survival of Serum-Starved Mouse Embryo and Human Fetus Fibroblasts", *Cellular Signalling* 12 (2000) 659-665.
Clubb et al., "The behavior of Infused Human Placental Alkaline Phosphatase in Human Subjects", *J. Lab & Clin. Med.* 66, 493-507, © 1965.
Angelucci et al., The Growth of Malignant and NonMalignant Human Cells is Modulated by a Human Placental Extract, *Anticancer Research* 19:429-436 (1999).
Beck et al., "Expression of Human Placental Alkaline Phosphatase in *Escherichia coli*", *Protein Expression and Purification* 5, 192-197 (1994).
Heimo et al., "Human Placental Alkaline Phosphatase: Expression in *Pichia pastoris*, Purification and Characterization of the Enzyme", *Protein Expression and Purification* 12. 85-92 (1998).
Kozlenkov et al., "Function Assignment to Conserved Residues in Mammalian Alkalie Phospatases", *The Journal of Biological Chemistry*, vol. 277, No. 25, pp. 22992-22999 © 2002.
Chang et al., "Human Placental Alkaline Phosphatase. An improved purification procedure and kinetic studies", *Eur. J. Biochem.*, 209. 241-247 © FEBS 1992.
Chang et al., "Modification of human placental alkaline phosphatase by periodate-oxidized 1,$N^6$-ethenoadenosine monophosphate", *Biochem. J.* 272, 683-690, © 1990.
Boukamp et al., "Normal Keratinization in a Spontaneously Immortalized Aneuploid Human Keratinocyte Cell Line", *The Journal of Cell Biology*, vol. 106, Mar. 1988, 761-771.
Carmichael et al., "Evaluation of a Tetrazolium-based Semiautomated Colorimetric Assay: Assessment of Chemosensitivity Testing", *Cancer Research*, 47, 936-942, Feb. 15, 1987.
Kottel et al., "Differential Release of Membrane-Bound Alkaline Phosphatase Isoenzymes from Tumor Cells by Bromelain", *Journal of Biochemical and Biophysical Methods*, 2 (1980) 325-330.
Juhasz et al., "Repopulation of Langerhans cells during wound healing in an experimental human skin/SCID mouse model", *Immunology Letters* 52 (1996) 125-128.
Wankell et al., "Impaired wound healing in transgenic mice overexpressing the activin antagonist follistatin in the epidermis", *The EMBO Journal*, vol. 20, No. 19, pp. 5361-5372, 2001.

* cited by examiner

*Primary Examiner*—David M. Naff
*Assistant Examiner*—Deborah K. Ware
(74) *Attorney, Agent, or Firm*—Faegre & Benson LLP

(57) ABSTRACT

Methods for stimulating proliferation of cells in the epidermis and dermis of mammalian skin are disclosed. The methods comprise the step of administering to an area of the skin a composition comprising a therapeutically effective amount of human placental alkaline phosphatase, or an active derivative. The composition can be administered topically or by injection. The invention also provides a regimen for restoring or maintaining the strength and thickness of aging skin, comprising periodically administering a composition by topical application. The invention further provides methods for stimulating proliferation of cells in the epidermis and dermis of transplanted skin. A composition for topical application is also provided by the invention.

29 Claims, 15 Drawing Sheets
(5 of 15 Drawing Sheet(s) Filed in Color)

USE OF PLACENTAL ALKALINE PHOSPHATASE TO PROMOTE SKIN CELL PROLIFERATION

TECHNICAL FIELD

A characteristic of aging skin is that skin cells, particularly fibroblasts, progressively lose their ability to proliferate. A reduction in the number of viable skin cells leads to reduced synthesis and secretion of collagen and other extracellular matrix proteins, resulting in thinning and wrinkling of the skin. Aging skin is further characterized by a decrease in flexibility and tensile strength. As a result, aging skin becomes more vulnerable to damage caused by external stress. Also, due to unfavorable changes in its texture, aging skin does not heal as well as young skin. Thus, restoration of a healthy structure to aging skin is important not only from a cosmetic point of view but also for health reasons.

Agents that enhance proliferation of epidermal and dermal cells in the skin, including fibroblasts and keratinocytes, are likely to be effective in restoring or maintaining the strength and thickness of aging skin. Fibroblast cells, located in the dermal layer, play important roles in mechanisms such as wound healing by, for example, producing components of the extracellular matrix like collagen and various cytokines, which, in turn, enhance the proliferation and migration of keratinocytes. Keratinocytes are located in the epidermal layer and form a barrier against the external environment.

There are many cosmetic products, some of which contain placental extracts, that can temporarily enhance the look and quality of skin. Such cosmetics and their ingredients have been discussed, for example, in two books [Begoun, P., "Don't go to the cosmetics counter without me." Beginning Press (1996); Winter, R,." Consumer's dictionary of cosmetic ingredients." Three Rivers Press (1994)]. Cosmetics are not assumed to change the structure of the skin (other than increasing hydration and inducing other small changes), and therefore do not require FDA approval. While certain light and UV sources have been proposed for skin care, and claims are occasionally made that these sources enhance proliferation of fibroblasts and epidermal cells, it is not clear if these effects are indeed produced by the presently available commercial cosmetic products.

Induction of relatively long-lasting changes in the skin requires agents and/or procedures that enhance the number of viable epidermal cells (keratinocytes) and dermal cells (particularly fibroblasts). This can be achieved by either enhancing the lifetime of these cells and/or stimulating their proliferation. Local treatment by known growth factors may be able to do that. However, most powerful growth factors are prohibitively expensive. Furthermore, virtually all growth factors stimulate the proliferation of either fibroblasts or keratinocytes, but not both.

Administration of placental alkaline phosphatase, one of the presently known four members of the alkaline phosphatase enzyme family [Millan, J. L. and Fishman, W. H., "Biology of human alkaline phosphatases with special reference to cancer." *Critical Reviews in Clinical Sciences* 32, 1-39 (1995)], has been reported to enhance both the proliferation [She, Q.-B., Mukherjee, J. J., Huang, J.-S., Crilly, K. S. and Kiss, Z., "Growth factor-like effects of placental alkaline phosphatase in human and mouse embryo fibroblasts." *FEBS Lett*. 469, 163-167 (2000)] and survival [She, Q.-B., Mukherjee, J. J., Chung, T. and Kiss, Z., "Placental alkaline phosphatase, insulin, and adenine nucleotides or adenosine synergistically promote long-term survival of serum-starved mouse embryo and human fetus fibroblasts." *Cellular Signalling* 12, 659-665 (2000)] of mouse embryo fibroblasts as well as fibroblast-like cells derived from the lung of human fetus.

Placental alkaline phosphatase is a member of the alkaline phosphatase group of enzymes that hydrolyze phosphate-containing compounds at alkaline pH. Mature placental alkaline phosphatase is a dimer of two identical glycosylated subunits. One source of placental alkaline phosphatase is human placenta, which synthesizes this enzyme during pregnancy so that toward the end of third term the enzyme's level in the placenta tissue and maternal/fetal blood becomes very high. Therefore, it is very unlikely that human placental alkaline phosphatase exerts toxic or pathological effects in human tissues. Subunits of human placental alkaline phosphatase ("PALP") have an approximate molecular weight of 66 kDa, as determined by gel electrophoresis.

A determination of an in vivo half-life for human PALP was reported in 1965 [Clubb, J. S., Neale, F. C. and Posen, S., "The behavior of infused human placental alkaline phosphatase in human subjects." *J. Lab. & Clin. Med.* 66, 493-507 (1965)]. In human subjects, injected PALP is reported to remain remarkably stable in the circulation, with an estimated biological half-life of about 7 days. In the reported experiments, PALP was injected as a minor constituent in a mixture of PALP and albumin obtained by extraction, without further purification. The authors reported that PALP up to serum concentration of 975 "King-Armstrong" (KA) units appeared metabolically inert, and hypothesized that PALP performs no measurable physiological function in circulation.

At least two potential therapeutic uses for human PALP have been reported. U.S. patent application Ser. No. 10/317,916, filed Dec. 12, 2002 and entitled "Placental Alkaline Phosphatase to Control Diabetes," and U.S. patent application Ser. No. 10/441,992, filed May 20, 2003 and entitled "Placental Alkaline Phosphatase to Control Diabetes," each of which is hereby incorporated by reference in its entirety, report the use of human PALP to reduce or control plasma glucose level. U.S. patent application Ser. No. 09/873,654, filed Jun. 4, 2001 and entitled "Compositions and Methods for Stimulating Wound Healing and Fibroblast Proliferation," which is hereby incorporated by reference in its entirety, reports the use of human PALP in combination with growth factors or serum factors for wound-healing compositions.

As mentioned above, it has recently been reported that administration of PALP can enhance both the proliferation and survival of mouse embryo fibroblasts as well as fibroblast-like cells derived from the lung of human fetus. Although mouse embryo fibroblasts and fibroblast-like cells from the fetus lung differ from human skin fibroblasts in many respects, those results indicated that PALP may be effective to enhance proliferation of human skin fibroblasts and even human keratinocytes. If so, PALP may be useful for enhancing proliferation of skin cells in vivo, and for promoting thicker and stronger skin.

In the past, many attempts were made to use various placenta extracts to improve the quality of skin (reviewed in Begoun, supra). However, all these extracts, like any tissue extract, presumably contained hundreds or even thousands of unknown components, including numerous proteins and hormones, many of which certainly exhibit uncharacterized biological activities. In fact, as reported recently [Angelucci, C., Lama, G., and Sica, G., "The growth of malignant and nonmalignant human cells is modulated by a human placental extract." *Anticancer Res*. 19, 429-436 (1999)], human placental extract contains both inhibitors and activators of cell growth whose effects depend on the incubation conditions in a highly unpredictable manner.

SUMMARY OF THE INVENTION

The experiments described herein demonstrate that administration of human placental alkaline phosphatase, but not other members of the alkaline phosphatase family, enhances proliferation of human skin fibroblasts and even human keratinocytes in vitro and in vivo. Thus, PALP may be used as an active component of skin care products designed to enhance thickness and strength of human skin.

The present invention provides a method for stimulating proliferation of cells in the epidermis and dermis of undamaged mammalian skin, by topically administering to an area of the skin a therapeutically effective amount of human placental alkaline phosphatase, or an active derivative thereof. In one embodiment of the method, the skin is human skin. In another embodiment of the method, a physiologically compatible carrier and human placental alkaline phosphatase or active derivative are administered to the skin.

The invention also provides a regimen for restoring or maintaining the strength and thickness of aging skin, by periodically administering by topical application to the skin a composition having an effective amount of human placental alkaline phosphatase, or an active derivative. In one embodiment of the regimen, the composition is applied once per day. In another embodiment of the regimen, the composition is applied about once per week.

Also provided by the invention is a method for stimulating proliferation of cells in the epidermis and dermis of mammalian skin, including the step of administering to the skin by injection a composition comprising a physiologically acceptable carrier, and a therapeutically effective amount of human placental alkaline phosphatase, or an active derivative thereof, dissolved or dispersed in the carrier. In one embodiment of the method, the carrier is a physiological saline solution. In another embodiment of the method, the mode of injection is selected from intravenous, subcutaneous, intramuscular, and intraperitoneal. In yet another embodiment, the mode of injection is intradermal.

The invention further provides a method for stimulating proliferation of cells in the epidermis and dermis of transplanted skin, including the step of topically administering to an area of the transplanted skin a therapeutically effective amount of human placental alkaline phosphatase, or an active derivative thereof. In one embodiment of the method, the transplanted skin is human skin. In another embodiment of the method, the transplanted skin has been transplanted onto a human host. Another embodiment of the method includes a step of topically administering a therapeutically effective amount of human placental alkaline phosphatase to an area of host skin that is adjacent to the transplanted skin.

The invention also provides a method for stimulating proliferation of cells in the epidermis and dermis of transplanted skin, including the step of administering to an area of the transplanted skin by injection a composition comprising a physiologically acceptable carrier, and a therapeutically effective amount of human placental alkaline phosphatase, or an active derivative thereof, dissolved or dispersed in the carrier.

A composition for topical application is also provided by the invention. In one embodiment, the composition includes either *vaselinum flavum* or *vaselinum album* and an amount of human placental alkaline phosphatase effective to stimulate proliferation of cells in the epidermis and dermis of mammalian skin. In another embodiment, the composition essentially contains *vaselinum flavum* or *vaselinum album* and human placental alkaline phosphatase. In a further embodiment, the composition essentially contains *vaselinum cholesterinatum* and human placental alkaline phosphatase.

BRIEF DESCRIPTION OF THE DRAWINGS

The patent or application file contains at least one photograph executed in color. Copies of this patent or patent application publication with color photographs will be provided by the Office upon request and payment of the necessary fee.

DETAILED DESCRIPTION OF THE INVENTION

Figure 1:
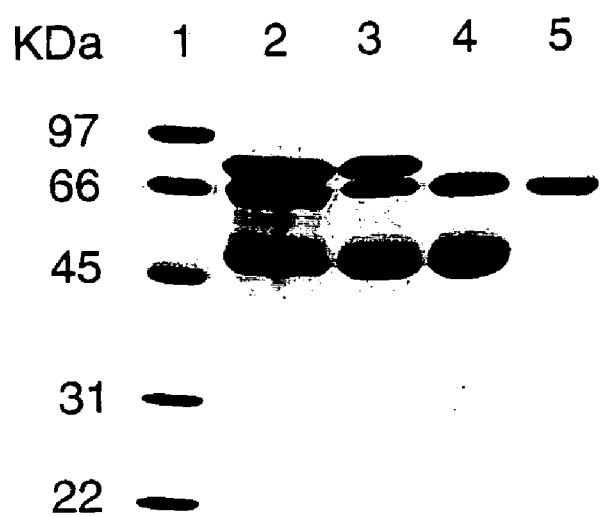
FIG. 1 shows a picture of a gel separation, demonstrating that homogeneous PALP used for the experiments described in Examples 2, 4, 9 and 10 does not contain any contaminating protein at a detectable level.

The experiments described herein demonstrate that topically or intradermally applied human placental alkaline phosphatase enzyme, but not other types of alkaline phosphatase enzymes, enhances the number of cells in both the epidermal and dermal layers of mouse dorsal skin, and of human skin transplanted onto mouse skin. Administration of human placental alkaline phosphatase was also found to enhance DNA synthesis and proliferation of HaCaT human keratinocytes and human skin fibroblasts in vitro. In one experiment, complete digestion of PALP by the protease bromelain failed to diminish, and instead slightly enhanced, the effect of PALP on DNA synthesis in fibroblasts. These observations imply that either human placental alkaline phosphatase or an active derivative thereof can be used as an active component of skin care products designed to thicken and strengthen aging skin and repair the epidermal and dermal layers of unhealthy skin of mammals and humans.

Another therapeutic application described herein for human placental alkaline phosphatase is to increase the likelihood of survival of transplanted skin by stimulating the proliferation of dermal and epidermal cells in the transplanted skin.

The Active Component

The methods and treatment regimens described herein include administration of a composition comprising human placental alkaline phosphatase, or an active derivative thereof. The composition generally comprises human PALP, or active derivative, in a carrier.

The active component in the methods and compositions of the present invention is human PALP, or an active derivative thereof. As used herein, the term "PALP" and the phrase "human PALP" are used interchangeably to refer to human placental alkaline phosphatase. As used herein, the phrase "active component" means a protein, enzyme, or peptide that, when administered at an appropriate concentration or quantity, is effective to stimulate proliferation of cells in the dermis or in the epidermis of mammalian skin, or is effective to restore strength or thickness to aging skin.

Placental alkaline phosphatase is a member of the alkaline phosphatase group of enzymes that hydrolyze phosphate-containing compounds at alkaline pH. Mature PALP is a dimer of two identical glycosylated subunits. Subunits of human placental alkaline phosphatase ("PALP") have an approximate molecular weight of 66 kDa, as determined by gel electrophoresis.

As is demonstrated by the Examples herein, whole PALP enzyme in its native state is not required to achieve a beneficial effect. Derivatives of PALP are therefore suitable as an active component for the practice of the present invention. For example, digestion of PALP by a protease, such as bromelain, provides an active derivative. Likewise, one who is skilled in the art may synthesize or develop an active derivative that is a smaller fragment of a PALP amino acid sequence and demonstrates efficacy similar to that of native PALP enzyme. By way of example, modification of a PALP amino acid sequence, or a sequence of smaller PALP peptides, by exchanging amino acids at critical sites to yield an active derivative may improve the beneficial effects disclosed herein. In the practice of the present invention, it is envisioned that modified PALP, smaller PALP-derived peptides, or modified PALP-derived peptides may be similarly effective or even more effective than the native PALP enzyme, and are each considered to be active derivatives.

Human PALP in solid form is available commercially from Sigma Chemical (St. Louis, Mo.), for example (Sigma catalog number P3895; CAS Registry Number 9001-78-9). Another commercial source of human PALP is Calbiochem (San Diego, Calif.; catalog number 524604).

Human PALP, or an active derivative, may also be obtained by chemical synthesis using conventional methods. For example, solid-phase synthesis techniques may be used to obtain synthetic PALP or an active derivative.

Recombinant methods of obtaining quantities of PALP (or an active derivative) are also suitable. Since the cDNA of PALP is available, recombinant protein can be produced by one of the many existing conventional methods for recombinant protein expression. PALP has been cloned and over-expressed in several cell lines, as described by Millan, et al. [Millan, J. L. and Fishman, W. H., "Biology of human alkaline phosphatases with special reference to cancer." *Critical Tev. Clin. Sci.* 22, 1-39 (1995)]. Production of recombinant PALP has been difficult to date, although low yields have been obtained from bacteria using *Escherichia coli* [Beck, R., and Burtscher, H., "Expression of human placental alkaline phosphatase in *Escherichia coli.*" *Protein Expression and Purification* 5, 192-197 (1994)] and from yeast using *Pichia pastoris* [Heimo, H., Palmu, K., and Suominen, I., "Human placental alkaline phosphatase: Expression in *Pichia pastoris*, purification and characterization of the enzyme." *Protein Expression and Purification* 12, 85-92 (1998)].

Recombinant PALP enzymes for the present study were prepared by a method described recently [Kozlenkov, A., Manes, T., Hoylaerts, M. F., and Millan, J. L., "Function assignment to conserved residues in mammalian alkaline phosphatases." *J. Biol. Chem.* 277, 22992-22999 (2002)].

A PALP preparation that is commercially available, synthesized, or produced by a recombinant method will generally contain impurities. Impure PALP preparations can be used as starting material to obtain homogeneous PALP by successive chromatographic steps, as described in detail in Example 1. Impure PALP preparations may also be used in formulating a composition for use in the practice of the present invention, so long as the composition comprises therapeutically effective amount of the active component, and any impurities are not toxic and do not interfere with the beneficial effects of the active component.

A preparation comprising human PALP may also be obtained by extraction from placental tissue. Human placenta synthesizes the enzyme during pregnancy, so that toward the end of third term the enzyme's level in the placenta tissue and maternal/fetal blood becomes very high. By way of example, a preparation may be obtained by butanol extraction of homogenized placenta. Other methods of extraction from placental tissue are also suitable.

Raw placental extracts that are not further enriched in PALP by using physical concentration methods cannot be expected to have physiological effects similar to those observed for a preparation of purified or homogeneous PALP, for at least two reasons. First, the relative concentration of PALP in an extract will be too low to expect a readily detectable effect in the skin. Second, raw placental extracts contain not only many different proteins but also other kinds of compounds, such as many lipids, proteolipids, carbohydrates, metals, vitamins, and the like.

Therefore, if placenta-derived PALP preparation is to be used in the practice of the present invention, a raw extract should be treated to enrich the concentration of PALP and obtain a purified preparation. A purified preparation will have a higher concentration of the active component than is found in a raw tissue extract, such as a raw placental extract. The term "purified" is used herein to encompass compositions that are obtained from a starting material by one or more purification steps (such as solvent extraction, column separation, chromatographic separation, etc.) that enrich the concentration of the active component, relative to the starting material. The term "purified" should not be construed to connote absolute purity.

The term "homogeneous" is used herein to indicate a composition that yields a single protein band in an electrophoretic gel separation, such as by the SDS-PAGE technique described in Example 1. The phrases "homogeneous human placental alkaline phosphatase" or "homogeneous PALP" therefore include compositions that contain predominantly PALP and yield a single band for PALP enzyme in an electrophoretic separation. Homogeneous PALP may be obtained, for example, from a raw placental extract (or from a purified preparation) by the purification procedures described in Example 1.

In the experiments described in the following Examples using placenta-derived PALP preparations, either a homogeneous PALP preparation obtained by a purification procedure described in Example 1 or a commercially available PALP preparation was employed. The commercial PALP preparation contains only a few proteins (see Example 1) as impurities, and the homogeneous PALP preparation contains no other proteins as detectable impurities. Thus, these preparations are qualitatively different from the previously used placenta extracts. Recombinant PALP preparations also contained no other proteins as detectable impurities.

As a result, the effects observed in the present experiments are qualitatively different from those that might have been observed previously by others using raw placental extracts. Based on any previously reported effects using placental extracts, the effects that were observed in the present experiments on the growth of skin cells using the PALP-containing compositions described herein could not have been predicted.

The likelihood of any toxic effects via local or intradermal application of PALP is insignificant because the protein's concentration in the circulation will be very small (probably undetectable). Even systematically applied, PALP is unlikely to be toxic, considering that the enzyme is produced by the placenta at a very high level during the second and third trimester of the pregnancy, and that the enzyme is readily detectable in the maternal blood. Furthermore, the in vivo half-life of PALP in humans is relatively short. The half-life has been measured as about 7 days [Clubb, J. S., Neale, F. C., and Posen, S., "The behavior of infused human placental alkaline phosphatase in human subjects." *J. Lab. & Clin. Med.* 66, 493-507 (1965)].

A further consideration in the practice of the invention is the degree of purity that is required for a PALP preparation that is to be administered to a human subject. An advantage of using a preparation comprising highly purified or homogeneous PALP in the methods and treatment regimens of the present invention is that possible side effects caused by contaminating proteins will not likely be an issue. However, impure PALP or PALP that is purified but not homogeneous (such as that comprising the commercially available human PALP from Sigma) may also be used in the compositions described herein, so long as no adverse effects are observed. Since each additional purification step results in significant loss of the enzyme, using a less pure PALP material for PALP preparations would be more cost-effective.

Compositions for Topical Administration

The present invention includes methods for stimulating proliferation of skin cells, and methods for restoring strength and thickness to aging skin, comprising a step of topically applying a composition comprising human placental alkaline phosphatase to the skin. The composition generally comprises human PALP or active derivative in a carrier. In a composition for administration to a human, the carrier should be a physiologically compatible or acceptable carrier.

For topical application, appropriate forms of the composition include, for example, creams, gels, lotions, unguents, emollients, colloidal dispersions, suspensions, emulsions, oils, sprays, foams, mousses, and the like. Compositions suitable for topical administration may also include, for example, liposomal carriers made up of lipids or special detergents.

Compositions suitable for topical application in the practice of the present invention generally include the active component as a minor ingredient, and the physiologically compatible carrier as a major ingredient. In some embodiments, the compositions may include one or more additives or enhancers, such as preservatives, buffers, moisture-control compounds, or antibiotics, for example. In other embodiments, the composition essentially contains the carrier and the active component. As used herein, the phrase "essentially contains" means that the composition has no other ingredient, other than the recited active component, that significantly stimulates proliferation of cells in the epidermis or dermis.

The carrier may be in any form appropriate for topical application to the skin. Any physiologically compatible carrier in which the active component is at least minimally soluble is suitable for topical compositions of the present invention. A physiologically acceptable carrier is one that is non-toxic, does not cause an adverse physical reaction upon administration, and in which the active component is sufficiently soluble or compatible so that the composition can provide an effective amount of the active component. The carrier should also provide a composition of appropriate consistency for topical administration and should be capable of achieving proper distribution of the active component to the treated tissue.

Suitable carriers generally include, for example, water, acetone, ethanol, ethylene glycol, propylene glycol, butane-1,3-diol, isopropyl myristate, isopropyl palmitate, mineral oil, mixtures thereof and the like. Buffered solutions can also serve as carriers.

In some embodiments, the topical composition is a gel. The gel may include as a carrier methyl cellulose, agar, vaseline or petrolatum, agarose, gelatin, calcium alginate or combinations thereof. By way of example, the active component can be incorporated into sterile 3% by weight methyl cellulose gel, 1% by weight agarose gel, 4% by weight gelatin gel, or 1 to 3% by weight calcium alginate.

Gels of more complex composition can also be formulated. In some embodiments, the carrier includes *vaselinum flavum* (yellow petrolatum), *vaselinum album* (white petrolatum), or *vaselinum cholesterinatum*. Commercially available *vaselinum cholesterinatum* consists of about 1.5 wt.-% cholesterol, about 5.0 wt.-% cerae lanae, and about 93.5 wt.-% *vaselinum flavum*.

Additives or enhancers may optionally be included in the topical compositions. The criterion for using an additive is that it increases, or at least does not significantly impair, the effectiveness of the active component in achieving the desired beneficial effect. Additives or enhancers in compositions for topical application may include various ingredients, for example, preservatives (such as parabens, quaternary ammonium compounds, alcohols, phenols, essential oils and the like), buffers, antioxidants (such as vitamin E), antimicrobials, vitamins, and moisture-control agents (such as glycerine, propylene glycol, and the like). Other potential additives include, for example, analgesics, anesthetics, anti-acne agents, anti-dermatitis agents, anti-pruritic agents, anti-inflammatory agents, anti-hyperkeratolytic agents, antiperspirants, anti-psoriatic agents, anti-seborrheic agents, anti-aging agents (such as retinoids), anti-wrinkle agents, skin-lightening agents, depigmenting agents, corticosteroids, additional tanning agents or hormones. Other additives may include, for example, colorants, sunscreens, emulsion stabilizers, preservatives, fragrances, humectants, waterproofing agents, viscosity modifying agents, and the like.

In one embodiment, the composition includes a penetration-enhancing additive that enhances penetration of the human placental alkaline phosphatase into the skin. Many conventional penetration enhancers are suitable in the practice of the invention. Non-limiting examples of suitable penetration enhancers include: sulfoxides such as dimethyl sulfoxide (DMSO); alcohols such as ethanol; polyols such as propylene glycol; surfactants such as sodium lauryl sulfate, lecithin, docusate sodium, and polysorbates; fatty acids such as lauric acid, myristic acid, palmitic acid, and stearic acid; esters such as isopropyl palmitate and isopropyl myristate; and amides such as urea.

Compositions for topical administration can be made using any number of suitable techniques. For example, a carrier, a preparation comprising an active component, and any optional additives can be mixed together using a commercial mixer to form a suspension, gel, solution or the like. Conventional methods known in the art are suitable. The compositions can be additionally processed after formulation. Sterilization, for example, can be conducted by filter sterilization, irradiation or the like. Methods for conducting these steps are also conventional in the art.

Both purified PALP preparations and homogeneous PALP preparations obtained from placental extracts can be used as the active component in the compositions described herein. The less pure the PALP preparation is, proportionally more of the PALP preparation must be used for the topical composition in order to provide an effective amount of the active component. Alternatively, a preparation comprising synthetic PALP or active derivative, or recombinant PALP or active derivative, can be employed as the active component. A preparation comprising an active component can also be derived from any of these PALP sources, such as by digestion of a PALP preparation with bromelain, for example.

In some embodiments, the composition comprises a therapeutically effective amount of human placental alkaline phosphatase, or active derivative thereof. The term "therapeutically effective amount" in this specification and in the claims indicates a dosage that is effective in, or is targeted to, either enhancing proliferation of fibroblasts or keratinocytes, or restoring or maintaining strength or thickness of aging skin. A therapeutically effective amount of an active component may vary based on the needs or tolerance of the individual subject, the degree to which the ability of fibroblasts or keratinocytes to proliferate has degenerated, the degree to which strength or thickness of the subject's skin has deteriorated, or other criteria evident to one of ordinary skill in the art.

In one embodiment of the invention, a composition for topical application includes a sufficient quantity of an active component to enhance proliferation of fibroblasts in the dermis. In another embodiment, a composition for topical application includes a sufficient quantity of an active component to enhance proliferation of keratinocytes in the epidermis. In yet another embodiment, topical administration of the composition enhances both proliferation of fibroblasts in the dermis and proliferation of keratinocytes in the epidermis.

Generally, the concentration of active component in a composition for topical application will be at least about 0.01 wt.-% and more suitably, between about 0.1 and about 1 wt.-%. In one embodiment, the composition comprises about 0.1 to about 0.5 wt.-% of the active component.

As one suitable composition for topical application, the invention provides a composition for topical application comprising either *vaselinum flavum* or *vaselinum album*, and an amount of human placental alkaline phosphatase effective to stimulate proliferation of cells in the epidermis and dermis of mammalian skin. The composition may include an additive that enhances penetration of the human placental alkaline phosphatase into the skin. In one embodiment, the composition contains about 0.1 to about 1 wt.-% human placental alkaline phosphatase. In another embodiment, the composition essentially contains *vaselinum flavum* and human placental alkaline phosphatase. In another embodiment, the composition essentially contains *vaselinum album* and human placental alkaline phosphatase. In yet another embodiment, the composition essentially contains *vaselinum cholesterinatum* and human placental alkaline phosphatase.

The invention further includes the use of human placental alkaline phosphatase in the manufacture of a topical composition effective to stimulate proliferation of cells in the epidermis and dermis of undamaged mammalian skin.

Topical Administration

The present invention provides a method for stimulating proliferation of cells in the epidermis and dermis of undamaged mammalian skin, comprising the step of topically administering to an area of the skin a composition comprising a therapeutically effective amount of human placental alkaline phosphatase, or an active derivative thereof.

The methods described herein are suitable for mammalian skin. The subject can be canine, porcine, or bovine, for example. Most suitably, the subject is human.

In the practice of the method, topical application of the composition is effective to stimulate proliferation of cells in the epidermis and dermis of the treated skin. Proliferation is stimulated when the rate of cell replication is increased (such as by an increase in the frequency of mitosis), relative to an untreated condition. In particular, proliferation of fibroblasts in the dermis may be enhanced. The methods also may be effective to stimulate proliferation of keratinocytes in the epidermis. The methods of the invention may also be effective to increase the viability of cells in the dermis or epidermis, or both.

The composition is applied to an undamaged area of skin. The term "undamaged" as used herein with reference to an area of skin indicates that the area of skin is free from wounds including cuts or punctures, abrasions, sores, scars, bruises, or burns of moderate- to high-degree that would require medical treatment. The methods of the invention are not intended for healing wounded or significantly damaged skin.

Topical administration can be accomplished via manual application of a composition such as a cream, a lotion, a gel and the like that includes the active component. A composition may also be applied by other means, such as by spraying, applying with a pad or towelette, etc. In some embodiments, a composition can be delivered by means of a dressing, bandage, patch, or other similar covering capable of releasing a therapeutically effective amount of the active component. Other methods of delivering the PALP compositions are also within the scope of this invention.

The method may suitably be practiced using any of the compositions described above, comprising a physiologically compatible carrier and human placental alkaline phosphatase, or an active derivative thereof.

In some experiments described herein, topical administration of PALP led to the stimulation of cells in the epidermis in the hair follicles. Although not studied in detail, this observation suggests that PALP may exert a positive effect on hair strength or even on hair growth.

Regimen for Restoring or Maintaining Strength and Thickness in Aging Skin

The invention also provides a regimen for restoring or maintaining the strength and thickness of aging skin, comprising periodically administering by topical application to the skin a composition comprising an effective amount of human placental alkaline phosphatase, or an active derivative.

A characteristic of aging skin is that skin cells, particularly fibroblasts, progressively lose their ability to proliferate. Aging skin is further characterized by a decrease in flexibility and tensile strength. Induction of relatively long-lasting changes in the skin requires agents and/or procedures that enhance the number of viable keratinocytes in the epidermis and fibroblasts in the dermis. Long-lasting changes can be achieved by either enhancing the lifetime of the cells or stimulating their proliferation, or both. Agents that enhance proliferation of epidermal and dermal cells in the skin, including fibroblasts and keratinocytes, are likely to be effective in restoring or maintaining the strength and thickness of aging skin.

In the practice of the regimen, any of the compositions described above may be used. The composition is applied topically to the skin, as described above. The composition is applied periodically over a period of time. As used with respect to the regimens described herein, the term "periodically" refers to repeated administration targeted to restoring or maintaining the strength and thickness of the skin, over the time of treatment. The term "periodically" includes repeated administration at fixed intervals, but also includes repeated administration over irregular intervals as is required by the subject's condition. The composition can be administered as needed. Alternatively, the composition can be administered two or more times a day. The frequency of administration of the composition can vary and depend on the type of skin, the location of the treated skin, the concentration of the active component in the composition, and the method used to administer the composition.

Generally, a therapeutically effective amount of the active component is administered. In the regimens of the invention, however, the effective amount of the active component that is administered does not need to be identical for each separate administration. More or less of the active component may be administered in separate administrations, as the subject's needs dictate. A medical professional supervising treatment can adjust administered doses to obtain desired results.

The frequency of application and the duration of the regimen will depend on the physiological state of the skin and, on the magnitude of response, and the level of satisfaction by the treated subject. In one embodiment of the regimen, the composition is applied once per day. In another embodiment of the regimen, the composition is applied about once per week.

For topical application, a recommended treatment schedule includes once-a-day treatment for the first week, three-times-a-week treatment for the second week, twice-a-week treatment for the third week, and once-a-week treatment for the following weeks, for a time period that is determined by the level of success.

While the important structural changes in the skin are expected to take place during the first three weeks after the regimen is commenced, a once-a-week treatment schedule may be desired after the first three weeks to maintain the improved texture of the skin. In other embodiments involving skin that is resistant to treatment or is badly deteriorated, the composition may be administered periodically for several months or more.

Administration by Injection

Also provided by the invention is a method for stimulating proliferation of cells in the epidermis and dermis of mammalian skin, comprising the step of administering to the skin by injection a composition comprising a physiologically acceptable carrier, and a therapeutically effective amount of human placental alkaline phosphatase, or an active derivative thereof, dissolved or dispersed in the carrier.

As a complement to the topical methods described above, other application methods, including various forms of injections, will also elicit the desired effects in the skin. In the case of injection, the active component will be transported to the skin either directly (such as for intradermal application or partly subcutaneous application) or via the blood supply (such as for intravenous, intraperitoneal, or subcutaneous applications). A composition comprising an active component may be administered via intravenous injection, intraperitoneal injection, subcutaneous injection, intradermal injection, intramuscular injection, or any other mode of delivery that ensures appropriate distribution and relative stability of the enzyme in the body.

For injection of a composition comprising an active component, the carrier can be any physiologically acceptable carrier that does not cause an undesirable physiological effect and is capable of ensuring proper distribution of the active component in the treated tissue. The active component is dissolved or dispersed in the physiologically acceptable carrier. Examples of carriers include physiological saline and phosphate-buffered saline. Alternatively, the active component may be enclosed in liposomes such as immunoliposomes, or other delivery systems or formulations as are known to the art may be employed. By way of example, the active component can be readily dissolved in physiological saline (0.9 M NaCl), or in any other physiologically competent carrier, to yield a solution for injection.

An injectable composition can be prepared by dissolving or dispersing a suitable PALP preparation in the carrier using conventional methods. As examples only, one suitable composition for the practice of the method comprises human PALP dissolved in a 0.9 N physiological salt solution to yield a PALP concentration of 10 mg/mL. Another suitable composition comprises human PALP dissolved in a 0.9 N physiological salt solution to yield a PALP concentration of 30 mg/mL.

The injectable composition can be modified by any number of additives, as listed above for the topical application, that can be dissolved or suspended in the composition and that are expected to enhance the effects of the active component or diminish any potential side effect.

In one embodiment of the method, the mode of injection is selected from intravenous, subcutaneous, intramuscular, and intraperitoneal. The mode of injection is selected to provide either local delivery (such as by intradermal application or partly subcutaneous application) or systemic delivery via the blood supply (such as for intravenous, intraperitoneal, or subcutaneous applications).

Since human PALP is a relatively large protein, and its actions involve multiple layers of skin, systemic administration is an appropriate mode of administration. Systemic administration of PALP is reported to be effective to modulate blood glucose levels, although the effect is not expected to be observed unless the subject already has an elevated blood glucose level (such as for a diabetic). In such cases, it may be desirable to avoid systemic administration in the practice of the methods of the present invention.

A common way to express a suitable dosage for systemic administration is grams of active agent per square meter of body surface area for the subject. Several formulas are known for estimating a human subject's body surface area, based on the human's height (in cm) and mass (in kg). Table 1 lists a variety of known formulas for estimating body surface area (BSA) proposed by researchers. Other suitable formulas may likewise be employed.

TABLE 1

Formulas for estimating body surface area (BSA).

| Author(s) | BSA formula |
| --- | --- |
| Du Bois and Du Bois | BSA (m$^2$) = Mass(kg)$^{0.425}$ × Height(cm)$^{0.725}$ × 0.007184 |
| Gehan and George | BSA (m$^2$) = Mass(kg)$^{0.51456}$ × Height(cm)$^{0.42246}$ × 0.02350 |
| Haycock | BSA (m$^2$) = Mass(kg)$^{0.5378}$ × Height(cm)$^{0.3964}$ × 0.024265 |
| Mosteller | BSA (m$^2$) = Mass(kg)$^{0.5}$ × Height(cm)$^{0.5}$ × 0.016666 |

In case of intravenous, intramuscular, intraperitoneal, or subcutaneous application, the subject may be administered about 1 to about 5 g/m$^2$ once daily. Alternatively, the subject may be administered about 0.2 to about 1.0 g/m$^2$ once daily.

In another embodiment, a subject may be administered by intravenous, intramuscular, intraperitoneal, or subcutaneous application about 0.2 to about 3.0 g/m$^2$ once or twice weekly. Alternatively, the subject may be administered about 0.2 to about 3.0 g/m$^2$ once biweekly by intravenous, intraperitoneal, or subcutaneous application.

In another embodiment, the subject may be administered about 1 to about 5 g/m$^2$ by intravenous, intramuscular, intraperitoneal, or subcutaneous application once daily for several days, with treatment then continued by less frequent applications of smaller doses.

If the PALP solution is injected locally, such as when the mode of injection is intradermal, aliquots of about 10 to about 100 μL per injection site may be administered. The concentration of the active component in the injectable composition may be in the range of about 1 to about 30 mg/mL. Alternatively, the concentration of the active component may be in the range of about 2 to about 10 mg/mL. In one embodiment, a plurality of injection sites is treated for one administration.

Intradermal application may be an especially effective mode of application in the practice of the present invention. Intradermal application may require use of less of the active component, as compared to other modes of injection. Also, for localized application the active component may be more effectively delivered or transported to the epidermal and dermal layers of the treated skin.

The invention further includes the use of human placental alkaline phosphatase in the manufacture of an injectable composition effective to stimulate proliferation of cells in the epidermis and dermis of undamaged mammalian skin.

Application to Transplanted Skin

The invention further provides a method for stimulating proliferation of cells in the epidermis and dermis of transplanted skin, comprising the step of topically administering to an area of the transplanted skin a composition comprising a therapeutically effective amount of human placental alkaline phosphatase, or an active derivative thereof. Any of the topical compositions described above are suitable in the practice of this method. The method may be effective to enhance the chance of survival of the transplanted skin (i.e., to increase the likelihood of a successful transplant).

In one embodiment of the method, the transplanted skin is human skin. In another embodiment of the method, the transplanted skin has been transplanted onto a human host. Another embodiment of the method includes a step of topically administering the composition to an area of host skin that is adjacent to the transplanted skin.

The invention further includes the use of human placental alkaline phosphatase in the manufacture of an topical composition effective to stimulate proliferation of cells in the epidermis and dermis of transplanted mammalian skin.

The invention also provides a method for stimulating proliferation of cells in the epidermis and dermis of transplanted skin, comprising the step of administering to an area of the transplanted skin by injection a composition comprising a physiologically acceptable carrier, and a therapeutically effective amount of human placental alkaline phosphatase, or an active derivative thereof, dissolved or dispersed in the carrier. The method may be effective to enhance the chance of survival of the transplanted skin (i.e., to increase the likelihood of a successful transplant).

In one embodiment of the method, the transplanted skin is human skin. In another embodiment of the method, the transplanted skin has been transplanted onto a human host. Another embodiment of the method includes a step of administering the composition by injection to an area of host skin that is adjacent to the transplanted skin. In another embodiment of the method, the mode of injection is intradermal.

The invention further includes the use of human placental alkaline phosphatase in the manufacture of an injectable composition effective to stimulate proliferation of cells in the epidermis and dermis of transplanted mammalian skin.

This invention may take on various modifications and alterations without departing from the spirit and scope thereof. Accordingly, it is to be understood that this invention is not to be limited to the above-described, but it is to be controlled by the limitations set forth in the following claims and any equivalents thereof. It is also to be understood that this invention may be suitably practiced in the absence of any element not specifically disclosed herein.

In describing preferred embodiments of the invention, specific terminology is used for the sake of clarity. The invention, however, is not intended to be limited to the specific terms so selected, and it is to be understood that each term so selected includes all technical equivalents that operate similarly.

EXAMPLES

Example 1

Purification and Spectrophotometric Assay of PALP

Human PALP (Type XXIV, 1020 units of total activity) in a partially purified form was obtained commercially from Sigma Chemical. A butanol extraction of placental tissue, followed by one or more chromatographic steps, was performed by Sigma Chemical to obtain the partially purified material. Butanol extraction inactivates most of the other placental proteins, including growth factors, but does not reduce either the mitogenic or the enzymatic activity of PALP.

As determined by sodium dodecyl sulfate-polyacrylamide gel electrophoresis (SDS-PAGE), the partially purified PALP obtained from Sigma Chemical (denoted "commercial PALP" herein) was not homogeneous and contained other proteins. FIG. 1 shows a picture of a gel separation of a preparation comprising commercial PALP without further purification, and other preparations of PALP of increasing purity. Separation of proteins was performed by conventional SDS-PAGE, and proteins were stained by coomassie blue stain. Lane 2 represents a preparation comprising commercial PALP, lanes 3 and 4 represent preparations comprising commercial PALP material after further purification steps (described below), and lane 5 represents a preparation of homogeneous PALP obtained by the complete purification procedure described below. Lane 1 contains various molecular mass standards for comparison.

As can be seen by reference to FIG. 1 at lane 2, the preparation comprising commercial PALP contained proteins other than PALP, and did not yield a homogeneous band in the electrophoretic separation. The preparation comprising commercial PALP contains at least three major proteins (one is PALP at approximately 66 kDa, while a band at approximately 52 kDa is $\alpha_1$-antitrypsin) and several minor proteins. Referring to lane 5 of FIG. 1, the preparation comprising homogeneous PALP (obtained by the complete purification procedure described below) apparently contains only PALP.

A purification procedure consisting of several steps was performed to further purify the commercially obtained PALP and to yield a homogeneous band in electrophoretic separation. The same purification procedure was followed that is described elsewhere [She, Q.-B., Mukherjee, J. J., Huang, J.-S., Crilly, K. S. and Kiss, Z., "Growth factor-like effects of placental alkaline phosphatase in human and mouse embryo fibroblasts." FEBS Lett. 469, 163-167 (2000)].

A solution of commercial PALP was prepared by dissolving 350 mg of commercial PALP into 10 mL of buffer A (0.1 M sodium acetate, 0.5 M NaCl, 1 mM $MgCl_2$, 1 mM $CaCl_2$, adjusted to pH 6.5). This solution was then further purified by successive Concanavalin A-Sepharose and Q-Sepharose chromatography, essentially following the procedure described elsewhere [Chang, T.-C., Huang, S.-M., Huang, T.-M. and Chang, G.-G., "Human placenta alkaline phosphatase: An improved purification procedure and kinetic studies." Eur. J. Biochem. 209, 241-247 (1992)], as follows.

The solution was run through a Concanavalin A-Sepharose column using buffer A as solvent. For elution, buffer A included 50 mM α-methyl-D-mannopyranoside. Active fractions collected from the effluent were pooled and dialyzed against buffer B (50 mM Tris-HCl at pH 7.7). SDS-PAGE separation of the collected and dialyzed fraction is shown in FIG. 1 at lane 3.

The collected and dialyzed fraction from the previous step was then passed through a Q-Sepharose column. The fraction of interest was eluted with buffer B using a linear gradient of 0-250 mM potassium phosphate at a pH of 7.5. The active fractions from the Q-Sepharose column were pooled and dialyzed against phosphate-buffered saline and concentrated by Amicon ultrafiltration. SDS-PAGE separation of the collected and dialyzed fraction is shown in FIG. 1 at lane 4, which demonstrates that at least two major proteins are still present in the fraction after dialysis.

Then, the collected and dialyzed fraction from the previous step was purified to homogeneity by t-butyl hydrophobic interaction chromatography (HIC). Prior to adding the fraction to a t-butyl HIC column, the fraction was made 2 M in ammonium sulfate, and pH was adjusted to 6.8. The 5 mL bed volume t-butyl HIC cartridge (BIO-RAD, Hercules, Calif.) was connected to a fast performance liquid chromatography (FPLC) system from PHARMACIA (Peapack, N.J.). The fraction was introduced to the HIC column, and the column was eluted with buffer C (100 mM sodium phosphate buffer, 2 M ammonium sulfate at pH 6.8). The column was eluted with buffer C until a first protein-containing fraction completely eluted, and then a negative gradient of 2 M-to-0 M ammonium sulfate in 100 mM sodium phosphate at pH 6.8 was passed over the column. The negative linear gradient was used to elute a second protein-containing fraction, which contained the enzymatically active PALP protein.

The enzymatically active fraction from the HIC separation was dialyzed against phosphate-buffered saline and concentrated by Amicon ultrafiltration. Presence and purity of the PALP enzyme in the fraction was confirmed by SDS-PAGE. After electrophoretic separation, the gel was stained using coomassie blue or silver stain for visual observation of protein bands. A single protein band was observed with an approximate molecular weight of 66 kDa (FIG. 1, lane 5). Identification of the PALP band by sequence analysis was performed by the Mayo Clinic Protein Core Facility (Rochester, Minn.).

PALP enzyme activity was assayed spectrophotometrically by monitoring the hydrolysis of 4-nitrophenylphosphate (as an increase in absorbance at 410 nm) at room temperature (22° C.) as described elsewhere [Chang, G.-G., Shiao, M.-S., Lee, K.-R. and Wu, J.-J., "Modification of human placental alkaline phosphatase by periodate-oxidized 1,$N^6$-ethenoadenosine monophosphate." Biochem. J. 272, 683-690 (1990)]. Activity analysis of 5-10 μg purified enzyme was performed in 1 mL incubation volume containing 50 mM $Na_2CO_3/NaHCO_3$, 10 mM $MgCl_2$, 10 mM 4-nitrophenylphosphate at pH 9.8. The extinction coefficient of 4-nitrophenol was taken as $1.62 \times 10^4$ $M^{-1}$ $cm^{-1}$. An enzyme activity of 1 U (unit) is defined as 1 μmol substrate hydrolyzed/min at 22° C. at pH 9.8.

Examples 2-10

Effects of PALP on Human Skin Cells In Vitro

In the following Examples, the effects of PALP on human cells lines derived from human skin are examined in vitro.

Partially purified human PALP (i.e., "commercial PALP") was purchased from Sigma Chemical, and purified as described in Example 1 to obtain homogeneous PALP.

(3-4,5-dimethylthiazol-2-yl)-2,5-diphenyltetrazolium bromide (MTT) was purchased from Sigma Chemical. [Methyl-$^{14}$H]thymidine (500 mCi/mmol) was purchased from DuPont NEN (Boston, Mass.). Tissue culture reagents, including Dulbecco's Modified Eagle's Medium ("DMEM"), Minimum Eagle's Medium ("MEM"), and fetal bovine serum ("FBS") were purchased from GIBCO-BRL (Rockville, Md.).

The human skin fibroblast cell lines CCD 39 SK, CCD 966 SK, CCD 1058 SK and CCD 1076 SK, derived respectively from one-week-old, 22-year-old, 52-year-old, and 38-year-old subjects, were purchased from American Type Culture Collection (Alexandria, Va.). The human skin fibroblast lines, maintained in 10% FBS-containing MEM, were used between 4-7 passages before they started to senesce. The immortalized human HaCaT keratinocyte cell line, isolated in 1988 [Boukamp, P., Petrussevska, R. T., Breitkreutz, D., Hornung, J., and Markham, A., "Normal keratinization in a spontaneously immortalized aneuploid human keratinocyte cell line." *J. Cell. Biol.* 106, 761-771 (1988)], was provided for these studies by Dr. Lajos Kemeny (Szeged University, Institute of Dermatology, Szeged, Hungary). HaCaT cells were maintained in 10% FBS-containing DMEM.

Example 2

Stimulation of DNA Synthesis by PALP in Fibroblasts and Keratinocytes

This Example describes the increased DNA synthesis in human skin fibroblasts and keratinocytes in the presence of PALP. Data for this Example is summarized in Table 2.

CCD 966 SK human skin fibroblasts (at about 40% confluency) were incubated in 2% FBS-containing MEM in 12-well plates (incubation volume 0.75 ml) in the absence or presence of 200 nM homogeneous PALP for 24 hours. 1 μCi/well of [methyl-$^3$H]thymidine was then added to the cells, which were then incubated for a subsequent 5 hours period; i.e. the total length of the incubation was 29 hours. At this point, cells in each well were still sub-confluent. The cells were washed twice with phosphate-buffered saline ("PBS"), then four times with 5% trichloroacetic acid, and finally twice with absolute ethanol.

The acid-insoluble material, which contained [$^3$H]thymidine-labeled DNA, was re-dissolved in 0.3 M sodium hydroxide. The $^3$H activity was then counted using a liquid scintillation spectrometer. In the results given below, "n" represents the number of independent samples that were measured to give the reported mean and standard error.

Using the above procedure, all $^3$H activity is associated with DNA. DNA in the control and PALP-treated cells contained 7,530±552 d.p.m./10$^6$ cells (n=3) and 11,790±1020 d.p.m./10$^6$ cells (n=3), respectively. This experiment indicated that PALP stimulates DNA synthesis in human skin fibroblasts.

The effect of homogeneous PALP (200 nM) on DNA synthesis was also determined in HaCaT keratinocytes using the same method as described above; the only difference was that the medium during the treatments (for a total of 29 hours) was 2% FBS-containing DMEM. DNA in the control and PALP-treated HaCaT cells contained 20,245±795 d.p.m./10$^6$ cells (n=3) and 34,770±995 d.p.m./10$^6$ cells (n=3), respectively.

TABLE 2

Stimulation of DNA synthesis in fibroblasts and keratinocytes.

| PALP | DNA Synthesis (d.p.m./10$^6$) | |
|---|---|---|
| | CCD 966 SK Fibroblasts | HaCaT keratinocytes |
| None | 7,530 ± 552 | 20,245 ± 795 |
| 200 nM | 11,790 ± 1020 | 34,770 ± 995 |

Examples 3-10

Effects of PALP on the Proliferation of HaCaT Cells and Fibroblasts In Vitro Since DNA synthesis is required for cell proliferation, and since the presence of PALP was found to stimulate DNA synthesis, the data suggested that the presence of PALP may also stimulate proliferation; i.e. the presence of PALP may increase the number of both fibroblasts and keratinocytes. This possibility was examined in the experiments described in the following Examples.

Overall, the experiments described in Examples 3 through 10 indicate that both commercial and homogeneous PALP exhibit similar positive effects on the proliferation of skin keratinocytes and fibroblasts in vitro. Depending on the incubation conditions, the positive effects were due to either increased survival or actual stimulation of proliferation. Regardless of the manner of action, commercial and homogeneous PALP preparations had similar stimulatory effects on the proliferation of both keratinocytes and fibroblasts.

These Examples show the quantitative effects of PALP on cell proliferation, as determined by the MTT assay first described by Carmichael, et al. [Carmichael, J., DeGraff, W. G, Gazdar, A. F., Minna, J. D., and Mitchell, J. B., "Evaluation of a tetrazolium-based semiautomated colorimetric assay: Assessment of chemosensitivity testing." *Cancer Res.* 47, 936-942 (1987)]. A fully automated version of this method was used in the experiments, as described below.

Either HaCaT cells or fibroblasts from the cell lines described above were seeded at 1000 cells/well in 96-microwell plates in 10% FBS-containing MEM (HaCaT cells) or DMEM (fibroblasts). After 24 hours, the medium was replaced with 2% FBS-containing fresh medium followed by treatments with commercial (Sigma) or homogeneous PALP for up to 3 days. At the end of the treatment the cultures still were subconfluent (~70-85% confluent).

The relative changes in the number of viable cells were determined by the MTT assay. This calorimetric assay is based on the ability of healthy cells (mostly the mitochondrial compartment) to reduce MTT to a blue formazan product. This technique is a widely used and accepted method to accurately determine the relative numbers of viable cells. For example, this is the official method used by the National Cancer Institute to screen anti-cancer drugs. In most cases, when the test agent does not strongly influence the oxidation-reduction balance of cells, the MTT assay is essentially a proliferation assay.

A MULTISKAN MS microplate reader purchased from Labsystems (Franklin, Mass.) was used to measure the formation of formazan as an increase in absorbance at a test wavelength of 540 nm and a reference wavelength of 690 nm. In the data analysis, data were expressed as mean values±standard deviation (S.D.) which the program calculated from 8 independent incubations from the same experiment. All experiments were repeated at least once (in each case again using 8 independent incubations) with similar results.

Example 3

Commercial PALP Enhances the Number of Viable HaCaT Cells

Figure 2:
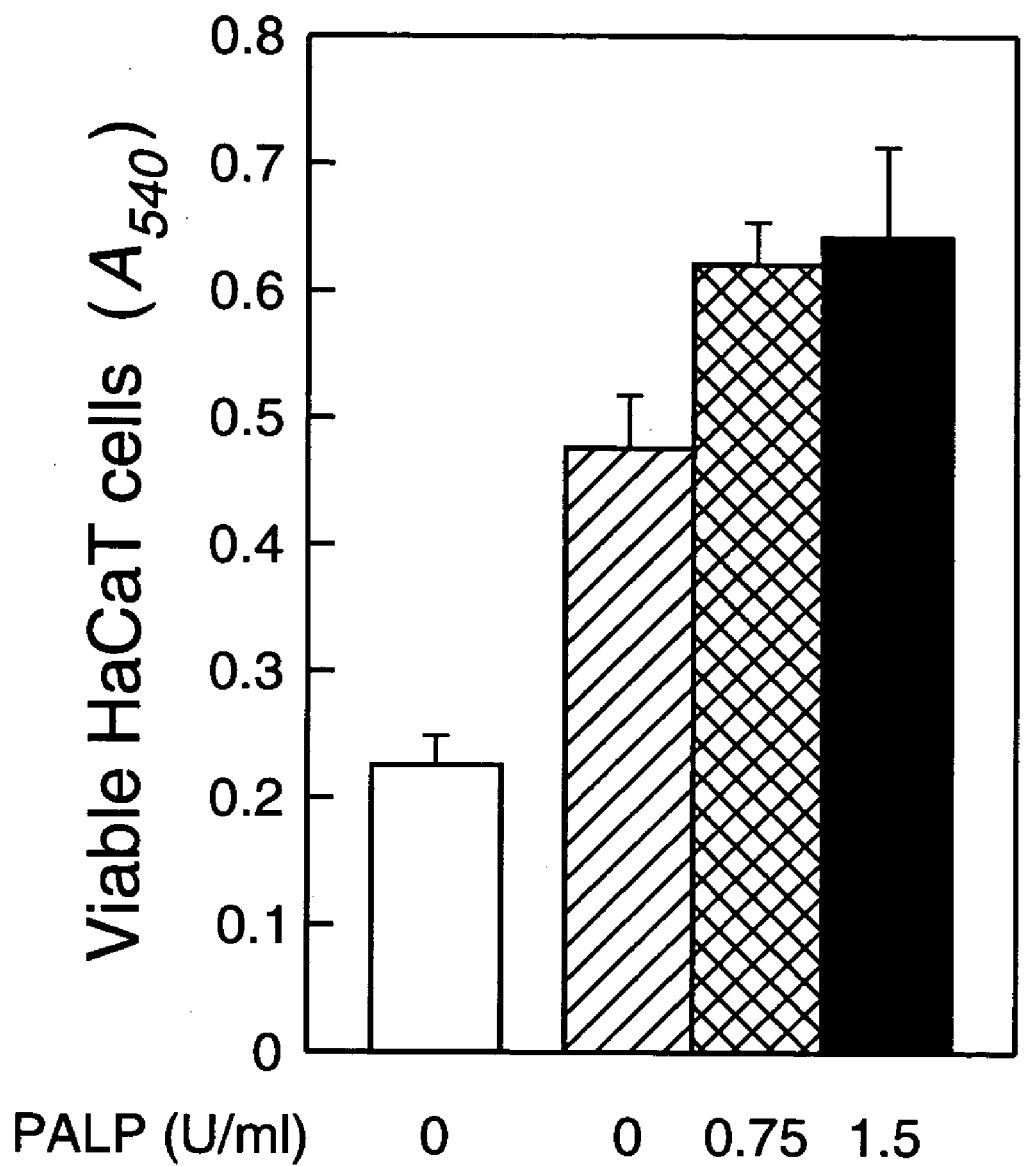
FIG. 2 demonstrates that administration of commercial PALP enhances the number of viable HaCaT epidermal cells in vitro.

Data for this Example is shown in FIG. 2. In this experiment, the medium on HaCaT cells was replaced with fresh 2% FBS-containing medium (□) and then cells were incubated for 72 hours in the absence (▨) or presence of 0.75 U/mL (▩) or 1.5 U/mL (■) of commercial (Sigma) PALP. "(▫)" indicates the relative number of cells at the start of the treatments. Data are reported as mean±S.D. of 8 incubations.

The results indicate that during the 72-hour incubation period the number of HaCaT cells were roughly doubled for the untreated cultures, and that 0.75-1.5 U/mL of commercial PALP further enhanced cell numbers 1.3- to 1.35-fold. These results were highly reproducible.

Comparative Example 3

Alkaline Phosphatase from Other Tissues does not Stimulate Proliferation of HaCaT Cells The effects of 0.25-2.5 U/mL of commercially available (Sigma-Aldrich Corp., St. Louis, Mo.) intestinal and kidney alkaline phosphatases were also tested on the proliferation of HaCaT cells under the conditions from Example 3. None of these alkaline phosphatase enzymes had detectable effects on the proliferation of HaCaT cells (experimental data not shown).

Example 4

Homogeneous PALP Enhances the Number of Viable HaCaT Cells

Figure 3:
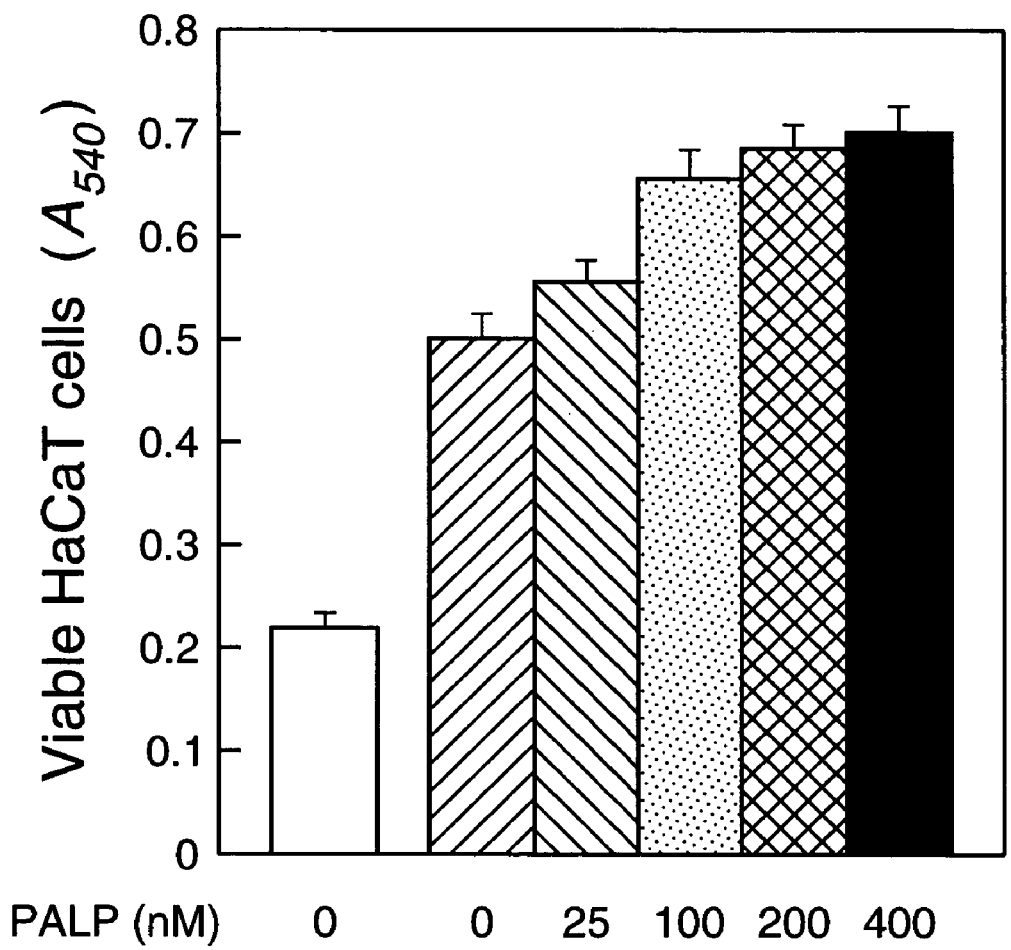
FIG. 3 demonstrates that administration of homogeneous PALP enhances the number of viable HaCaT epidermal cells in vitro.

Data for this Example is shown in FIG. 3. This experiment with HaCaT cells was performed exactly as described in Example 2, except that homogeneous PALP was used at the following concentrations; 0 (▨), 25 nM (▩), 100 nM (▫), 200 nM (▨), and 400 nM (■). "(▫)" again indicates the relative number of cells at the start of the treatments.

While 25 nM PALP had little detectable effect, 100-400 nM concentrations of PALP clearly enhanced the number of cells 1.31 to 1.4-fold. Thus, the stimulatory effects observed for commercial PALP on the proliferation of keratinocytes is reproduced using homogeneous PALP.

Example 5

Effects of Commercial PALP on the Proliferation of CCD 39 SK Fibroblasts

Figure 4:
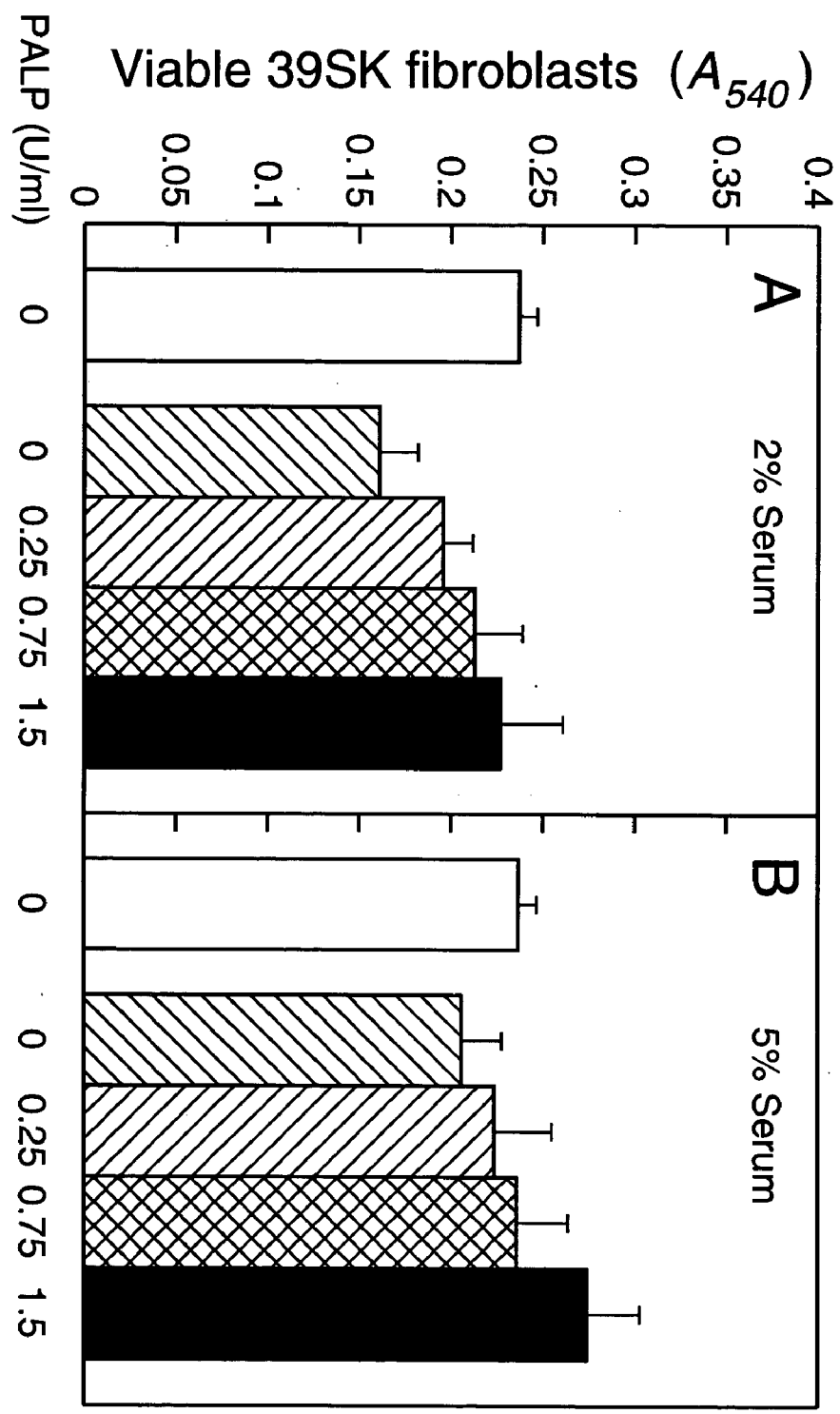
FIG. 4 demonstrates that administration of commercial PALP enhances the number of viable CCD 39 SK human skin fibroblasts in vitro.

Data for this Example is shown in FIG. 4. CCD 39 SK human skin fibroblasts were treated for 72 hours, in the presence of 2% FBS (FIG. 4A) or 5% FBS (FIG. 4B), with the following concentrations of commercial (Sigma) PALP: 0 (▨), 0.25 U/mL (▩), 0.75 U/mL (▨), or 1.5 U/mL (■). "(▫)" indicates the relative number of cells at the start of the treatments. Data are reported as mean±S.D. of 8 incubations.

In the presence of 2% serum, the CCD 39 SK cells did not survive well, as indicated by a decrease in viable cell numbers. The presence of PALP in either 2% serum (FIG. 4A) or 5% serum (FIG. 4B) largely prevented such decrease, with the preventative effect becoming greater at higher concentration of PALP. In the presence of 5% serum (FIG. 4B), 1.5 U/mL of PALP slightly enhanced cell numbers. These results clearly indicate that in CCD 39 SK fibroblasts the major action of PALP was to enhance cell survival in the absence of serum factors.

Example 6

Effects of Commercial PALP on the Proliferation of CCD 966 SK Fibroblasts

Figure 5:
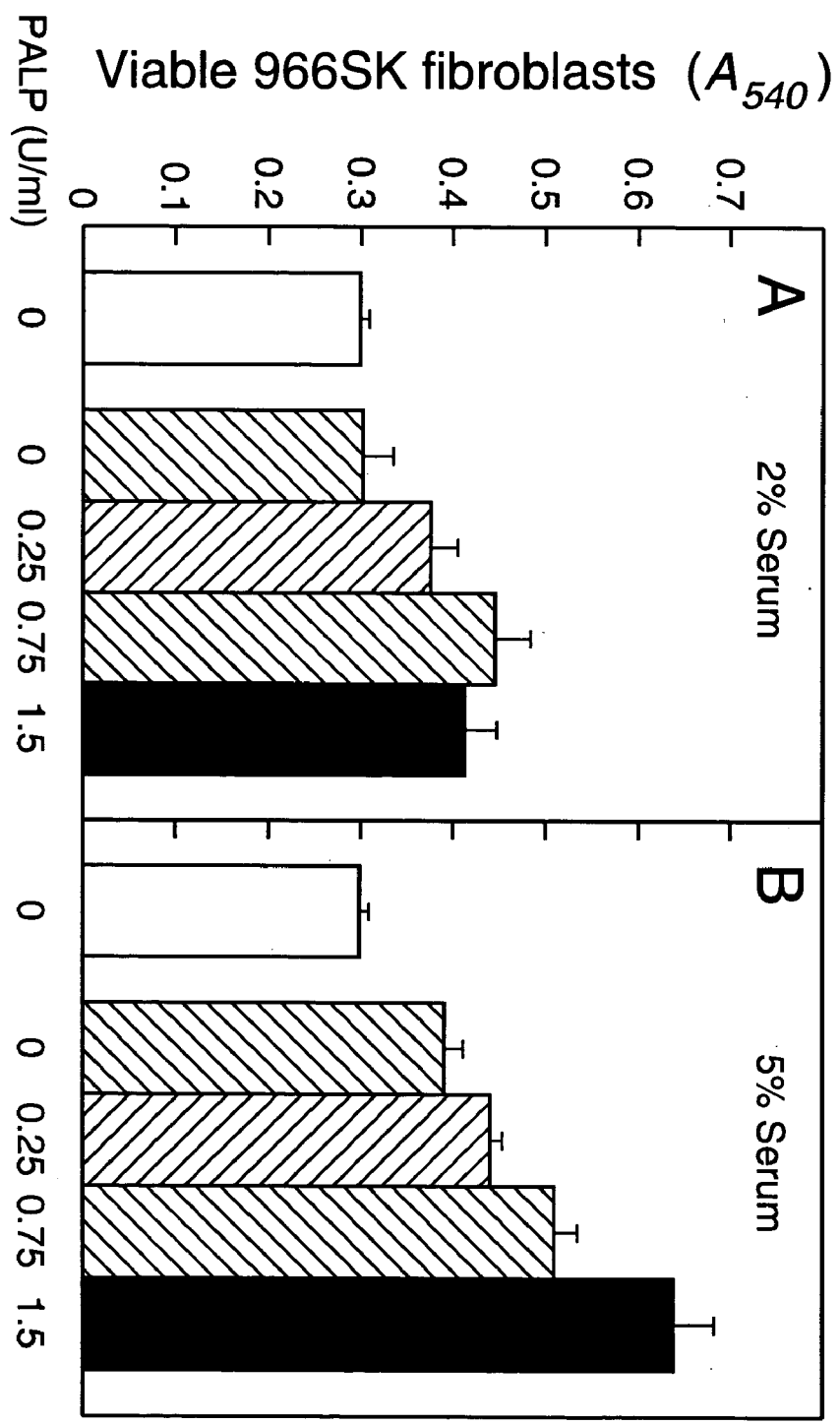
FIG. 5 demonstrates that administration of commercial PALP enhances the number of viable CCD 966 SK human skin fibroblasts in vitro.

Data for this Example is shown in FIG. 5. CCD 966 SK human skin fibroblasts were treated for 72 hours, in the presence of 2% FBS (FIG. 5A) or 5% FBS (FIG. 5B), with the following concentrations of commercial (Sigma) PALP: 0 (▨), 0.25 U/mL (▩), 0.75 U/mL (▨), or 1.5 U/mL (■). "(▫)" indicates the relative number of cells at the start of the treatments. Data are reported as mean±S.D. of 8 incubations.

In the presence of 2% serum, the CCD 966 SK cells survived well, but did not proliferate. In the presence of 5% serum the cells exhibited only modest proliferation.

The presence of PALP at 0.75-1.5 U/mL concentrations in 2% (FIG. 5A) and 5% (FIG. 5B) serum clearly enhanced the cell numbers. The results were reproduced in three other experiments performed as described above. Observation of the stimulation of cell proliferation is consistent with the observed stimulatory effect of PALP on DNA synthesis in CCD 966 SK cells as reported in Example 2.

Example 7

Effects of Commercial PALP on the Proliferation of CCD 1058 SK Fibroblasts

Figure 6:
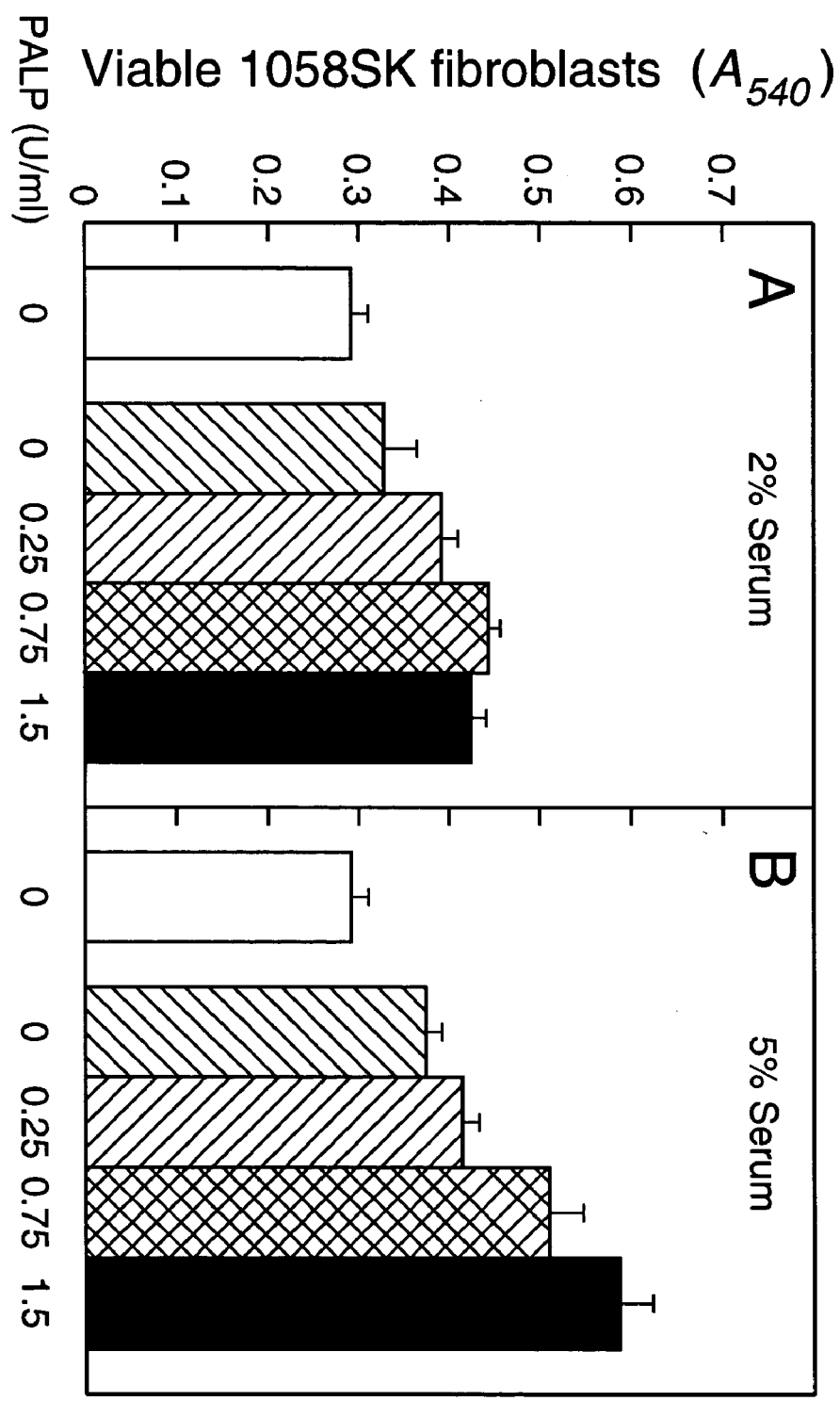
FIG. 6 demonstrates that administration of commercial PALP enhances the number of viable CCD 1058 SK human skin fibroblasts in vitro.

Data for this Example is shown in FIG. 6. CCD 1058 SK human skin fibroblasts were treated for 72 hours, in the presence of 2% FBS (FIG. 6A) or 5% FBS (FIG. 6B), with the following concentrations of commercial (Sigma) PALP: 0 (▨), 0.25 U/mL (▩), 0.75 U/mL (▨), or 1.5 U/mL (■). "(▫)" indicates the relative number of cells at the start of the treatments. Data are reported as mean±S.D. of 8 incubations.

The CCD 1058 SK cells responded to serum and PALP-containing serum in a manner similar to the CCD 966 SK cells. Namely, the CCD 1058 SK cells survived well in the presence of 2% serum, while they proliferated only in the presence of 5% serum. The presence of PALP at 0.75-1.5 U/mL concentrations in 2% (FIG. 6A) and 5% (FIG. 6B) serum clearly enhanced the cell numbers.

Example 8

Effects of Commercial PALP on the Proliferation of CCD 1076 SK Fibroblasts

Figure 7:
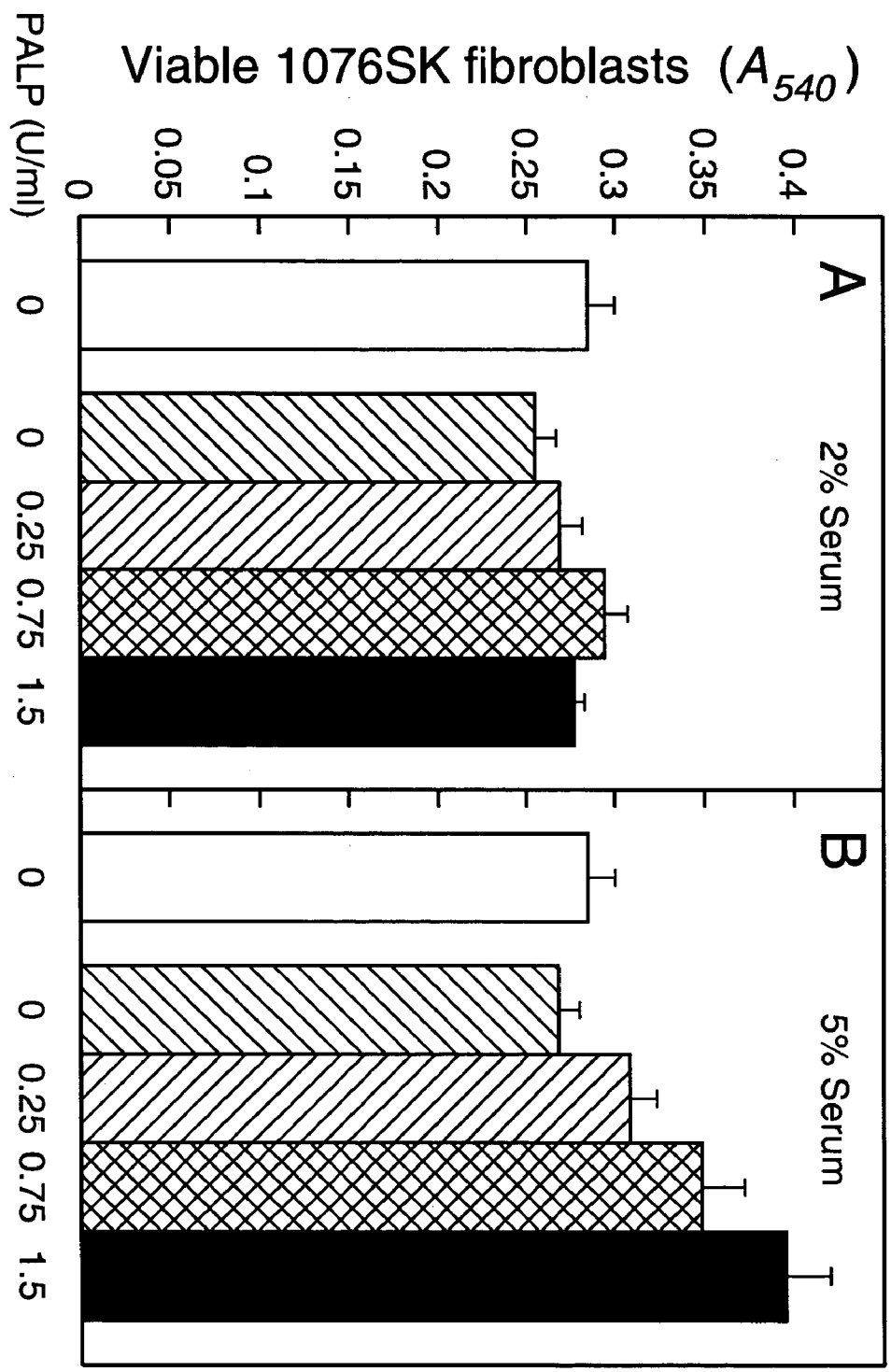
FIG. 7 demonstrates that administration of commercial PALP enhances the number of viable CCD 1076 SK human skin fibroblasts in vitro.

Data for this Example is shown in FIG. 7. CCD 1076 SK human skin fibroblasts were treated for 72 hours, in the presence of 2% FBS (FIG. 7A) or 5% FBS (FIG. 7B), with the following concentrations of commercial (Sigma) PALP: 0 (▨), 0.25 U/mL (▩), 0.75 U/mL (▨), or 1.5 U/mL (■). "(▫)" indicates the relative number of cells at the start of the treatments. Data are reported as mean±S.D. of 8 incubations.

The CCD 1076 SK cells responded to serum and PALP-containing serum in a manner similar to the CCD 39 SK cells. Namely, in the presence of 2% serum, the CCD 1076

SK cells did not survive well as indicated by a small decrease in viable cell numbers. The presence of PALP in 2% serum (FIG. 7A) appeared to prevent such decrease. The presence of PALP in 5% serum caused proliferation of the cells, with 1.5 U/mL of PALP in 5% serum actually enhancing cell numbers by about 1.4-fold (FIG. 7B).

Example 9

Effect of Homogeneous PALP on the Proliferation of CCD 966 SK Fibroblasts

Figure 8:
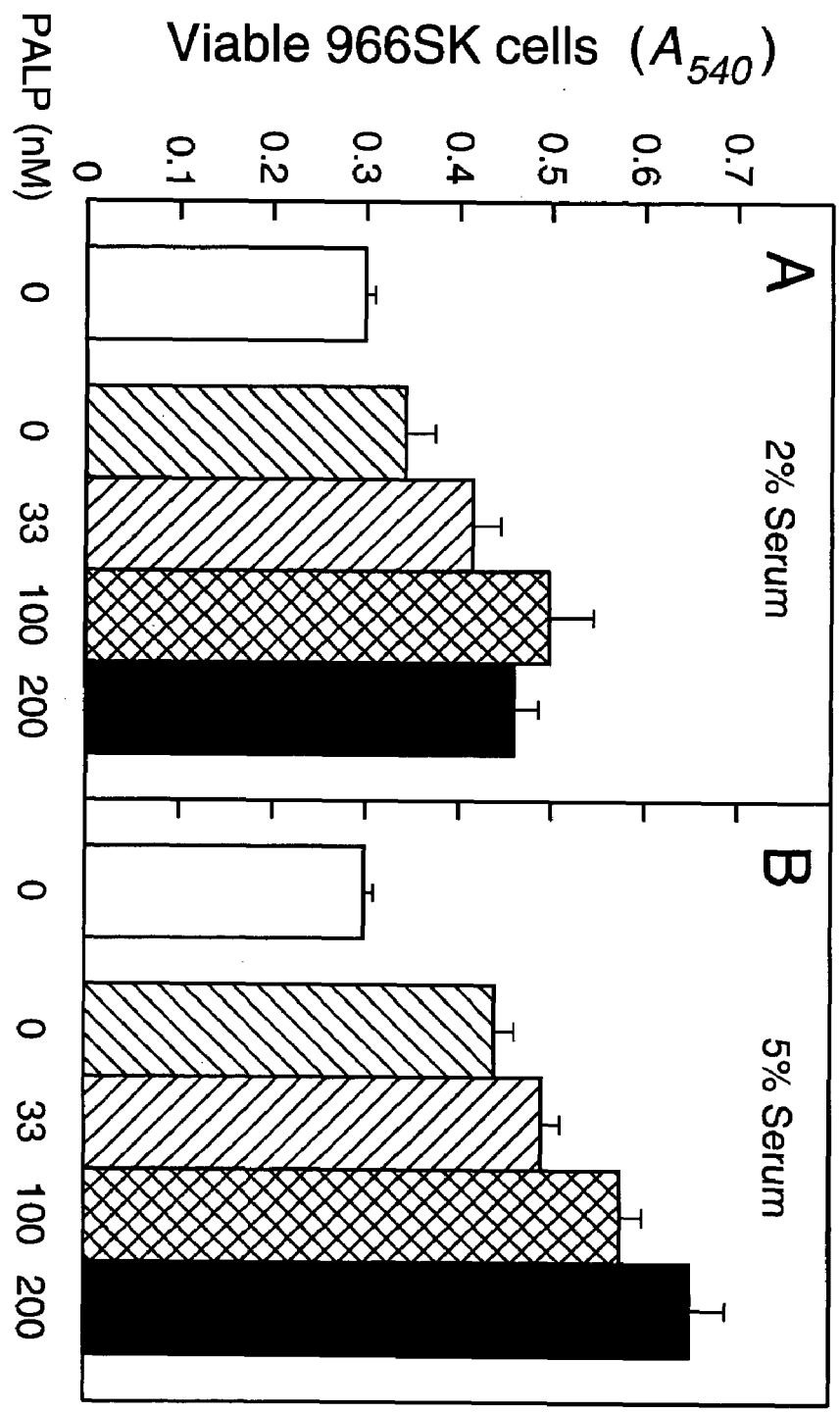
FIG. 8 demonstrates that administration of homogeneous PALP enhances the number of viable CCD 966 SK human skin fibroblasts in vitro.

Data for this Example is shown in FIG. 8. CCD 966 SK fibroblasts were treated for 72 hours, in the presence of 2% FBS (FIG. 8A) or 5% FBS (FIG. 8B), with the following concentrations of homogeneous PALP: 0 (▨), 33 nM (▧), 100 nM (▨), or 200 nM (■). "(□)" indicates the relative number of cells at the start of the treatments. Data are reported as mean±S.D. of 8 incubations.

For the CCD 966 SK cell line, the presence of 33-200 nM PALP clearly enhanced cell numbers in both 2% serum and 5% serum.

Comparative Example 9

Alkaline Phosphatase from Other Tissues does not Stimulate Proliferation of CCD 966 SK Fibroblasts The effects of 0.25-2.5 U/mL of commercially available (Sigma-Aldrich Corp.) intestinal and kidney alkaline phosphatases were also tested on the proliferation of CCD 966 SK fibroblasts under the conditions from Example 9. None of these alkaline phosphatases had detectable effects on the proliferation of CCD 966 SK fibroblasts (data not shown).

Example 10

Effect of Homogeneous PALP on the Proliferation of CCD 1058 SK Fibroblasts.

Figure 9:
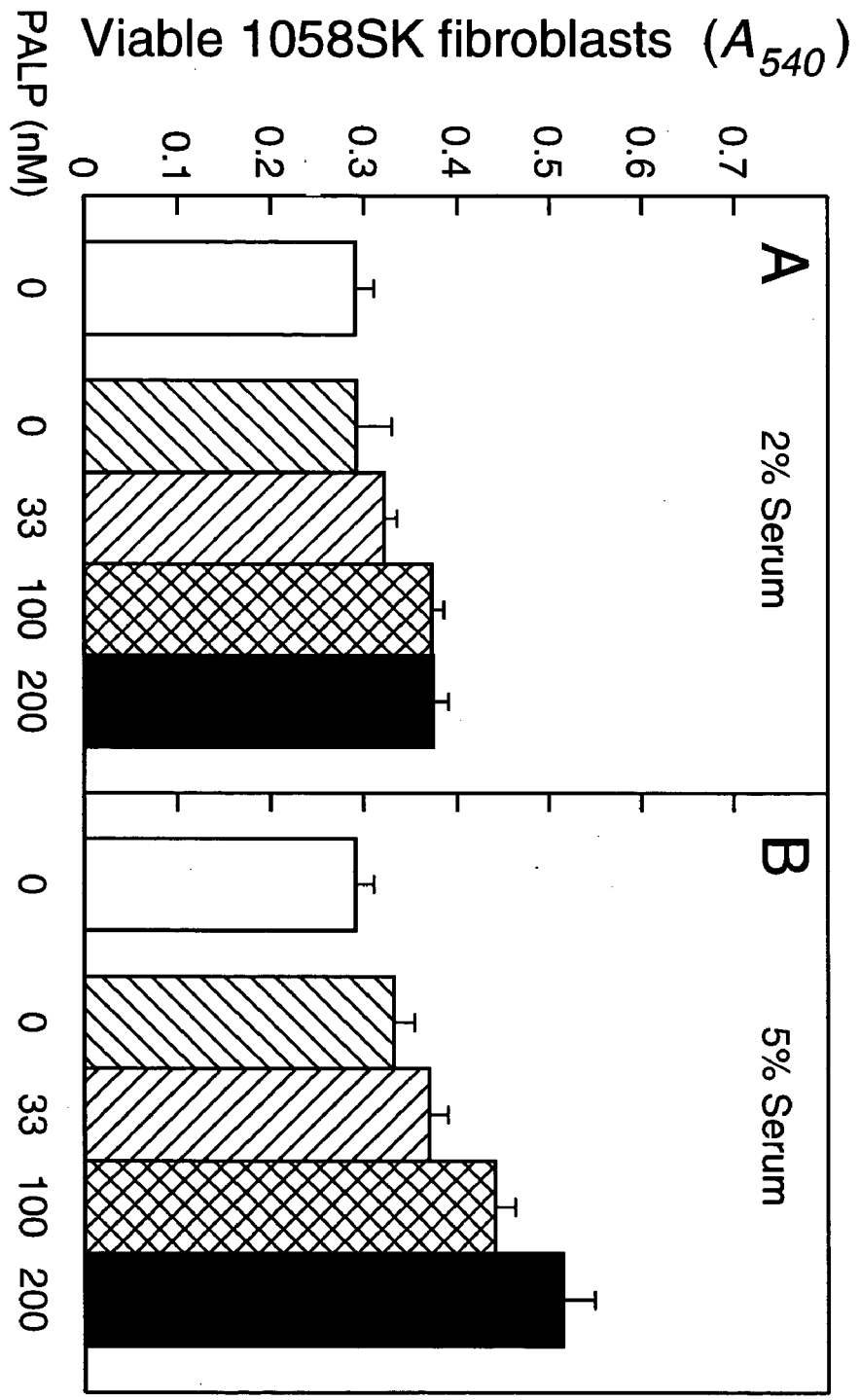
FIG. 9 demonstrates that administration of homogeneous PALP enhances the number of viable CCD 1058 SK human skin fibroblasts in vitro.

Data for this Example is shown in FIG. 9. CCD 1058 SK fibroblasts were treated for 72 hours, in the presence of 2% FBS (A) or 5% FBS (B), with the following concentrations of homogeneous PALP: 0 (▨), 33 nM (▧), 100 nM (▨), or 200 nM (■). "(□)" indicates the relative number of cells at the start of the treatments. Data are reported as mean±S.D. of 8 incubations.

For the CCD 1058 SK cell line, the presence of 33-200 nM PALP clearly enhanced cell numbers in both 2% serum and 5% serum.

Comparative Example 10

Alkaline Phosphatase from Other Tissues does not Stimulate Proliferation of CCD 1058 SK Fibroblasts The effects of 0.25-2.5 U/mL of commercially available (Sigma-Aldrich Corp.) intestinal and kidney alkaline phosphatases were also tested on the proliferation of CCD 1058 SK fibroblasts under the conditions from Example 10. None of these alkaline phosphatases had detectable effects on the proliferation of CCD 1058 SK fibroblasts (data not shown).

Overall, the experiments under Examples 3-10 indicated that administration of either commercial PALP or homogeneous PALP elicits similar positive effects on the proliferation of both skin keratinocytes and fibroblasts in vitro. Depending on the incubation conditions, the positive effects were due to either increased survival or actual stimulation of proliferation. Regardless of the manner of action, administration of commercial PALP or homogenous PALP had similar stimulatory effects on the proliferation of both keratinocytes and fibroblasts. Therefore, it is a reasonable inference that if commercial PALP stimulates skin cell proliferation in vivo, it is mainly due to the action of PALP and not a contaminating protein.

Examples 11-13

Stimulation of Cell Proliferation by PALP is Elicited by Digested PALP or Mutated PALP Example 11

Digestion of PALP by Bromelain

Bromelain (BRL) is a protease which was previously shown to effectively digest PALP leading to the formation of fragments of lower molecular mass [Kottel, R. H. and Hanford, W. C., "Differential release of membrane-bound alkaline phosphatase isoenzymes from tumor cells by bromelain." Biochem. Biophys. Methods 2, 325-330 (1980)]. Based on this observation, bromelain was used to digest commercial PALP to determine if digestion by a protease can generate a smaller PALP fragment which is able to stimulate DNA synthesis.

Figure 10:
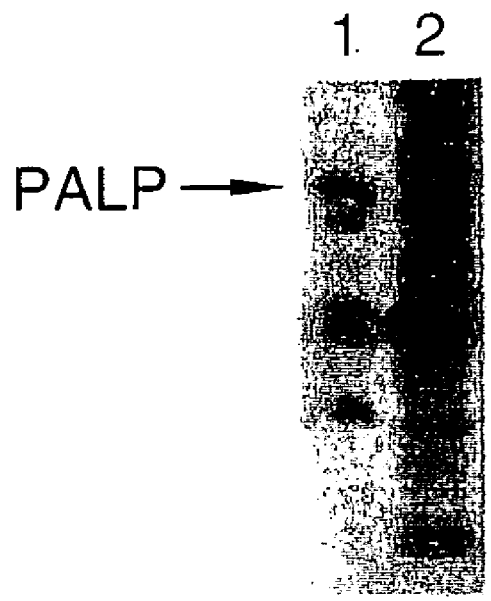
FIG. 10 shows a picture of a gel separation demonstrating that digestion of human PALP with bromelain results in the formation of a major fragment and several smaller fragments, concomitant with the disappearance of native PALP enzyme.

A preparation comprising 20 U/mL commercial PALP and 0.1 mg/mL of BRL (Sigma-Aldrich) in 1 mL of 25 mM Tris-HCl (pH 7.4) buffer was incubated at 37° C. for 2 hours. FIG. 10 shows a picture of a gel separation (obtained by SDS-PAGE using 7.5% polyacrylamide) with undigested commercial PALP in lane 1 and BRL-digested PALP in lane 2. It is clear that, after digestion with 0.01 mg/mL of BRL, no detectable amount of the original PALP molecule remains.

Example 12

Effects of Bromelain-Digested PALP on DNA Synthesis in CCD 1058 SK Fibroblasts

This Example describes the increased DNA synthesis in human skin fibroblasts in the presence of both untreated and bromelain-digested PALP. Data for this Example is summarized in Table 3.

CCD 1058 SK human skin fibroblasts (at about 40% confluency) were incubated for 24 hours in 2% FBS-containing MEM in 12-well plates (incubation volume 0.75 ml) under the following conditions: (a) in the presence of 1.5 U/mL commercial (Sigma) PALP; and (b) in the presence of 1.5 U/mL commercial (Sigma) PALP that had been treated with bromelain for 2 hours, as described in Example 1.

Then 1 µCi/well of [methyl-$^3$H]thymidine was added to the cells for a subsequent period of 5 hours, so that the total length of the incubation period was 29 hours. At this point, cells in each well were still sub-confluent. Incubation was stopped, and labeled DNA was quantified as described in Example 2.

DNA in control (untreated) fibroblasts, and DNA in fibroblasts incubated with commercial PALP (condition (a)) contained 14,300±960 d.p.m./$10^6$ cells (n=3) and 38,160±1,720 d.p.m./$10^6$ cells (n=3) of [$^3$H]thymidine, respectively. DNA in fibroblasts treated with a corresponding amount of bromelain alone, and DNA in fibroblasts incubated with PALP treated with bromelain (condition (b)) contained 10,950±370 d.p.m./$10^6$ cells (n=3) and 50,640±860 d.p.m./$10^6$ cells (n=3) of [$^3$H]thymidine, respectively.

Finally, simultaneous addition of 100 μg/mL of PALP-specific polyclonal antibody (Polyclonal Rabbit anti-Placental Alkaline Phosphatase, Zymed Laboratories, South San Francisco, Calif.) to cells incubated with 1.5 U/mL of commercial PALP reduced the incorporation of [$^3$H]thymidine into DNA to 18,340±4,140 d.p.m./$10^6$ cells (n=3).

TABLE 3

Stimulation of DNA synthesis in CCD 1058 SK fibroblasts.

| Treatment | DNA Synthesis (d.p.m./$10^6$) |
|---|---|
| Untreated | 14,300 ± 960 |
| 1.5 U/mL commercial PALP | 38,160 ± 1,720 |
| Bromelain | 10,950 ± 370 |
| 1.5 U/mL commercial PALP, digested with bromelain | 50,640 ± 860 |
| 1.5 U/mL commercial PALP, plus 100 μg/mL antibody | 18,340 ± 4,140 |

The results indicate that digestion of PALP with bromelain did not reduce, in fact slightly enhanced, the stimulatory effect of PALP on DNA synthesis.

It should be noted that CCD 1058 SK fibroblasts were somewhat more sensitive to the stimulatory mitogenic effects of PALP than CCD 966 SK cells. However, this might simply reflect that while 1058 SK cells were used at passage 5, 966 SK cells (Example 2) were used at passage 7. Increase in passage number in case of human skin fibroblast lines (which senesce after 8-12 passages) is usually accompanied by a concomitant reduction in the effects of mitogens, such as PALP.

Apart from this difference, this experiment indicates that smaller fragments of PALP may be as effective, or even more effective, than the native PALP enzyme in stimulating mitogenesis in skin cells. The data obtained for experiments including the PALP-specific antibody further prove that DNA synthesis was stimulated by PALP and not by an impurity present in the commercial PALP preparation.

Example 13

Effects of Recombinant PALPs on the Proliferation of Human Skin Fibroblasts

In this Example, recombinant PALP enzymes were used to further demonstrate that the effects of homogeneous PALP on human fibroblast proliferation were not caused by an undetected impurity present in homogeneous PALP. Recombinant wild-type and mutant enzymes were produced for these experiments exactly as described by Kozlenkov, et al. [Kozlenkov, A., Manes, T., Hoylaerts, M. F., and Millan, J. L., "Function assignment to conserved residues in mammalian alkaline phosphatases." *J. Biol. Chem.* 277, 22992-22999 (2002)].

To simplify the recovery and purification of the recombinant enzymes, the glycosylphosphatidylinositol anchoring sequence of PALP was replaced by the FLAG octapeptide, and both the wild-type and mutant enzymes were expressed as secreted, epitope-tagged, enzymes. Site-directed mutagenesis, a conventional method for creating mutant proteins, was used to replace Histidine-358 with alanine. Such point mutation was reported by Kozlenkov, et al. to result in the complete loss of the catalytic enzyme activity, and this result was confirmed during the experiments described herein.

The effects on the proliferation of CCD 966 SK human fibroblasts for the wild-type (w-PALP) and mutant (m-PALP) recombinant enzymes were compared. The cell proliferation assay was performed essentially as described in Examples 3 through 10. Briefly, CCD 966 SK fibroblasts were seeded at 1000 cells/well in 96-microwell plates in 10% FBS-containing MEM. After 24 hours, the medium was replaced with 2% FBS-containing fresh medium, followed by treatments for 48 hours with either 100 nM recombinant wild-type or mutant PALP, and either 500 nM insulin or no insulin.

At the end of the treatments the cultures were about 80% confluent. The relative changes in the number of viable cells were determined by the MTT assay as indicated earlier. Data obtained is reported in Table 4. Data are based on 6 incubations (6 separate wells) and are reported as mean±S.D. The $A_{540}$ value for control cells at the time of starting the treatments was 0.360±0.027.

TABLE 4

Stimulation of fibroblast proliferation by recombinant PALP enzymes.

| | Cell Proliferation ($A_{540}$) | |
|---|---|---|
| PALP | no insulin | 500 nM insulin |
| None | 0.415 ± 0.054 | 0.577 ± 0.063 |
| w-PALP, 100 nM | 0.584 ± 0.047 | 0.621 ± 0.035 |
| m-PALP, 100 nM | 0.607 ± 0.053 | 0.636 ± 0.041 |

The results clearly show that both the wild-type and mutant recombinant enzymes enhanced the number of viable fibroblasts. The effect was only slightly higher in the presence of insulin for both enzymes. This experiment indicates that PALP stimulates cell proliferation, and that its stimulatory effect does not require the catalytic (phosphate group-hydrolyzing) enzyme activity. This further demonstrates the likelihood that smaller fragments of the PALP enzyme lacking the sequence around the catalytic site may be effective in stimulating cell proliferation, and therefore useful as active components for the compositions and methods described herein.

Examples 14-18

Effects of Commercial PALP on the Proliferation of Skin Cells In Vivo

These Examples demonstrate that in mouse skin, or in human skin transplanted onto the back of mice, application of commercial PALP on the skin enhances cell numbers both in the epidermis and dermis and results in significant thickening of the epidermis. Comparison of data obtained with mouse and human skin indicates that both types of skin respond to PALP by increasing the thickness of epidermis and the number of dermal cells. In addition, in both cases PALP also enhanced the growth of epidermal layer in the hair follicles, suggesting that PALP may promote hair growth in human skin as well.

In all experiments, seriously compromised immune deficient ("SCID") mice were used, which were bred at the Department of Dermatology, University Medical School of Debrecen (Debrecen, Hungary). The mice were housed and handled under specific pathogen-free ("SPF") conditions. They were used at 8-14 weeks of age.

Most of the subsequent experimental procedures, outlined below, were described in detail by Juhasz et al. [Juhasz, I., Simon, Jr., M., Herlyn, M., and Hunyadi, J., "Repopulation of Langerhans cells during wound healing in an experimental human skin/SCID mouse model." *Immunology Letters* 52, 125-128 (1996)]. The histological analysis by hematoxylin/eosin and detection of proliferating cells by labeling with bromodeoxyuridine are conventional procedures and have been described, for example, by Wankell et al. [Wankell, M., Munz, B., Hubner, G., Hans, W., Wolf, E., Goppelt, A. and Werner, S., "Impaired wound healing in transgenic mice overexpressing the activin antagonist follistatin in the epidermis." *The EMBO J.* 20, 5361-5372 (2001)].

An area of approximately 1.5 $cm^2$ on the dorsal skin of the subject mouse was shaved and treated with a cream consisting of 3.6 mg of commercial PALP mixed in 1 g of *vaselinum cholesterinatum*; this composition is designated for the rest of application as "PALP cream." For each application, 100 mg PALP cream was massaged into 1 $cm^2$ shaved skin area.

In some experiments, the treated skin was human skin that had been grafted onto the mouse skin. Human foreskin from children at ages between 0.5-6 years were obtained from the Department of Urology, University Medical School of Debrecen. For the grafting procedure, performed at the Department of Dermatology, University Medical School of Debrecen, a mouse (at age 6-8 weeks) was anesthetized with inhalatory anesthetic methoxyflurane. SCID mice were utilized to minimize the risk of rejection of transplanted tissue by the host mouse. A circular graft bed of approximately 1.5 $cm^2$ was prepared on the lateral abdomen of the mouse by removing skin down to the fascia. The full-thickness donor foreskin was placed onto the wound bed and held in place with 5-0 monofilament sutures. The transplantation site was covered with a layer of non-stick gauze (CUTICERIN, available from Beiersdorf of Hamburg, Germany) and an adhesive bandage soaked with physiological saline and sutured to the dorsal and ventral skin of the animal with a surgical stitch. An additional layer of surgical tape was then applied. The transplanted skin was treated with the PALP cream after 4-6 weeks of the surgery.

For histology, skin samples were excised from the treated areas (for topical treatment) or within 1-3 mm distance from the site of injection (for treatment by intradermal injection). The excised skin samples were fixed in 4% paraformaldehyde in phosphate-buffered saline and embedded in paraffin so that several consecutive cross-sections could be made. Sections (6 μm) were stained with hematoxylin/eosin ("H&E"). At least 20 sections derived from 4 animals were evaluated for the effectiveness of each type of treatment.

Example 14

Figure 11:
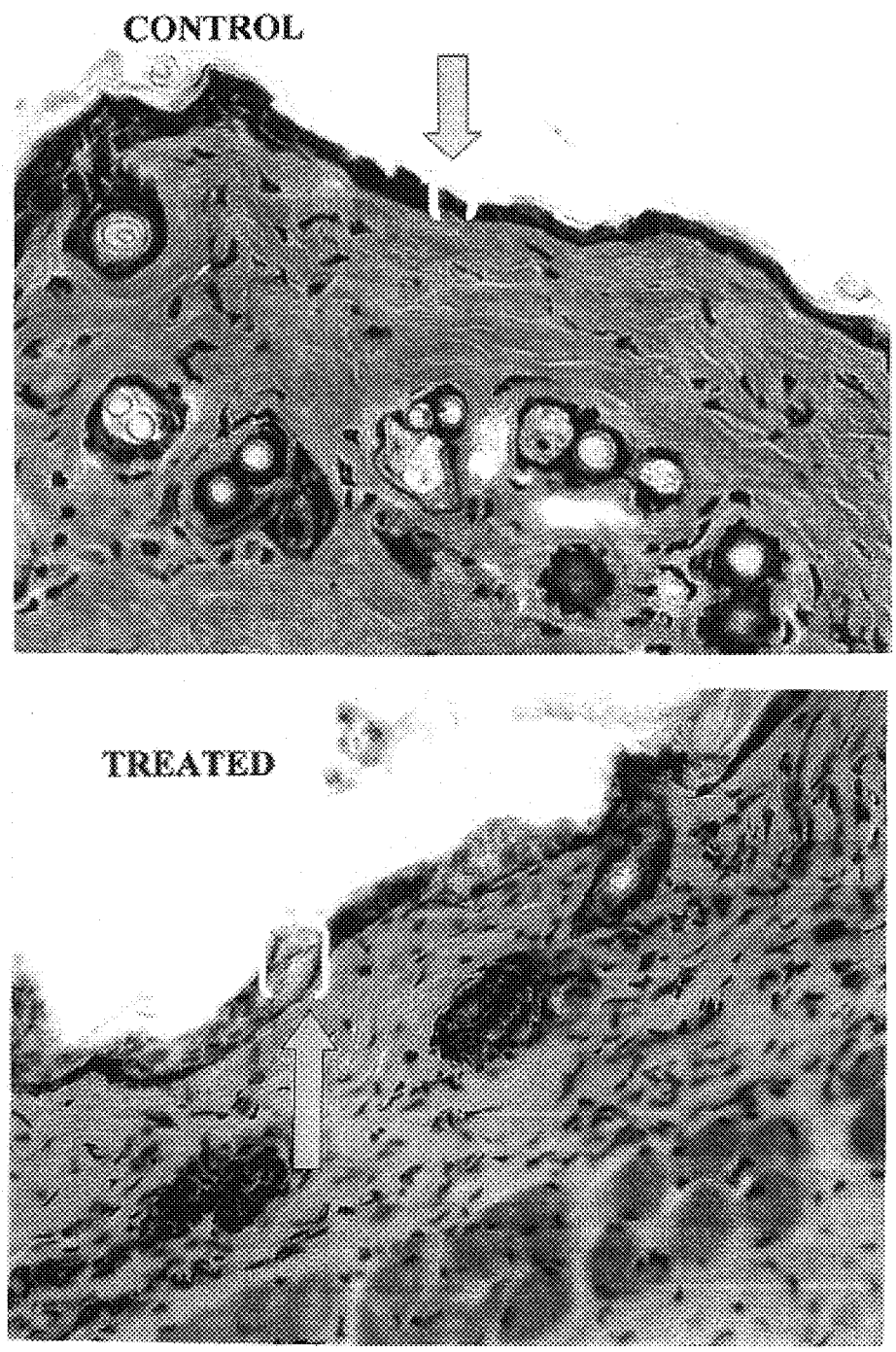
FIG. 11 (color) is a picture of a histological sample showing that topical application of PALP-containing cream on mouse back on Day 1 and 6 enhances the number of epidermal cells and the number of dermal cells.

Alterations in the Structure of Mouse Skin After Two Treatments with the PALP Cream A picture of a histological sample from this Example is shown in FIG. 11. In the experiment, *vaselinum cholesterinatum* (upper "control" panel) or PALP cream (lower "treated" panel) was applied on the dorsal skin on Day 1 and on Day 6, and tissue sections were stained with H&E on Day 10. The sections shown are representative of at least 20 sections. Comparison of the two sections indicate that even such limited treatment with PALP cream clearly enhanced the thickness of the epidermal layer (indicated by the intensity of blue color) resulting from the increased numbers of epithelial cells. The PALP cream also enhanced the number of cells, mostly fibroblasts, in the underlying dermis (lower panel).

Example 15

Figure 12:
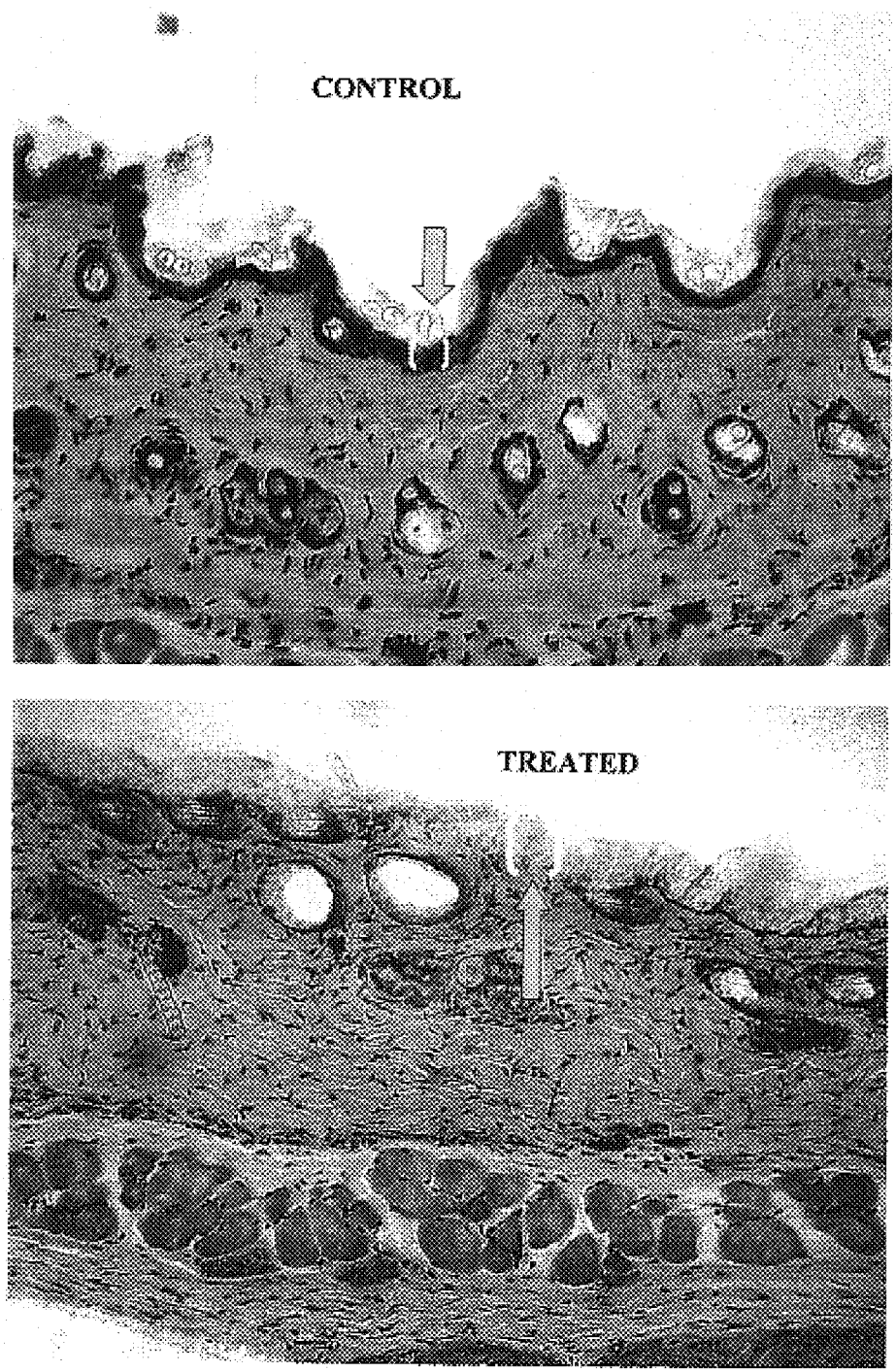
FIG. 12 (color) is a picture of a histological sample showing that topical application of a PALP-containing cream on mouse dorsal skin on every other day over 10 days enhances the number of epidermal cells and the number of dermal cells.

Alterations in the Structure of Mouse Skin After Five Treatments with the PALP Cream A picture of a histological sample from this Example is shown in FIG. 12. In this experiment, *vaselinum cholesterinatum* (upper "control" panel) or PALP cream (lower "treated" panel) was applied on the dorsal skin on Days 1, 3, 5, 7, and 9, followed by sectioning and staining of tissue samples on Day 10. The sections shown are representative of at least 20 sections. More frequent application of the PALP cream led to more pronounced thickening of the epidermal layer (indicated by the intensity of blue color and the arrow). The cream also clearly enhanced the number of cells (mostly fibroblasts) in the underlying dermis.

Example 16

Figure 13:
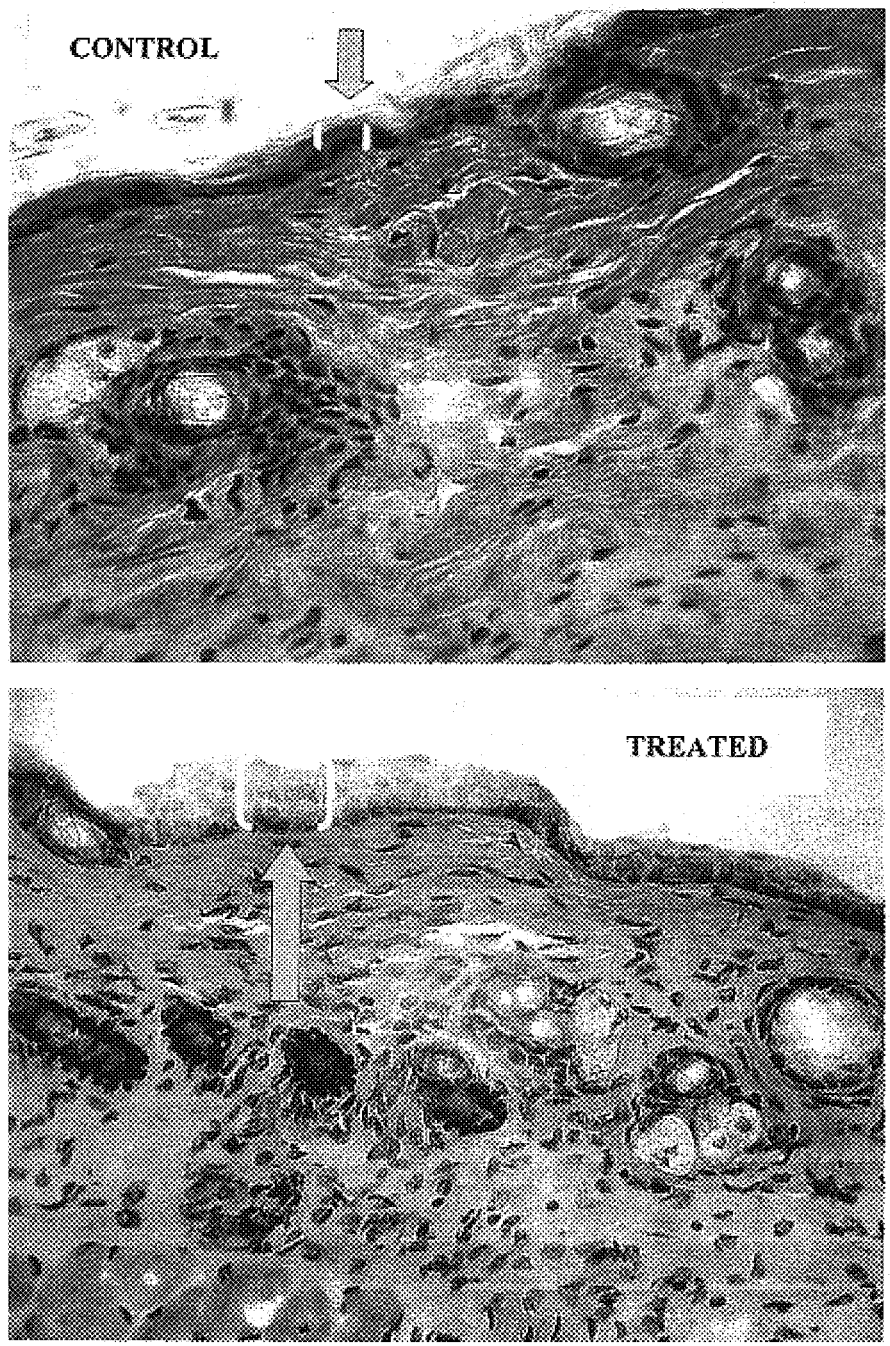
FIG. 13 (color) is a picture of a histological sample showing that topical application of PALP-containing cream on mouse dorsal skin on every fourth day over 20 days enhances the number of epidermal cells and the number of dermal cells.

Alterations in the Structure of Mouse Skin After Less Frequent, but More Prolonged, Treatments with the PALP Cream A picture of a histological sample from this Example is shown in FIG. 13. In this experiment, *vaselinum cholesterinatum* (upper "control" panel) or PALP cream (lower "treated" panel) was applied on the dorsal skin on Days 1, 4, 8, 12 and 16, followed by sectioning and staining of tissue samples on Day 20. The sections shown are representative of at least 20 sections. The representative picture in the lower panel demonstrates that less frequent application over a more prolonged time period also greatly increases the thickness of epidermis (indicated by the intensity of blue color and the arrow), as a consequence of increased cell number, as well as the number of dermal cells.

It is noteworthy that with all three different treatment schedules, the epidermis in the hair follicles also exhibited increased activity (judged from increased intensity of blue color around the follicles). Although not studied in detail, this observation suggests that PALP may exert a positive effect on hair strength or even on hair growth.

Example 17

Effect of Intradermally Delivered PALP on the Structure of Mouse Skin

Figure 14:
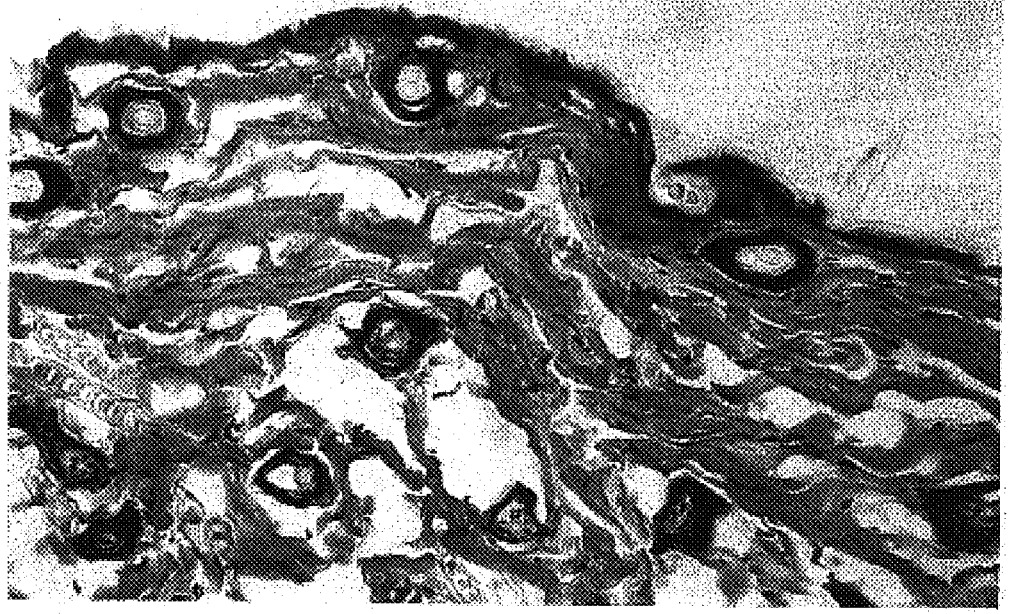
FIG. 14 (color) is a picture of a histological sample demonstrating that in mouse dorsal skin, intradermally administered PALP induces thickening of the epidermal layer and prevents edema induced by a physiological saline (control) solution.
Figure 14:
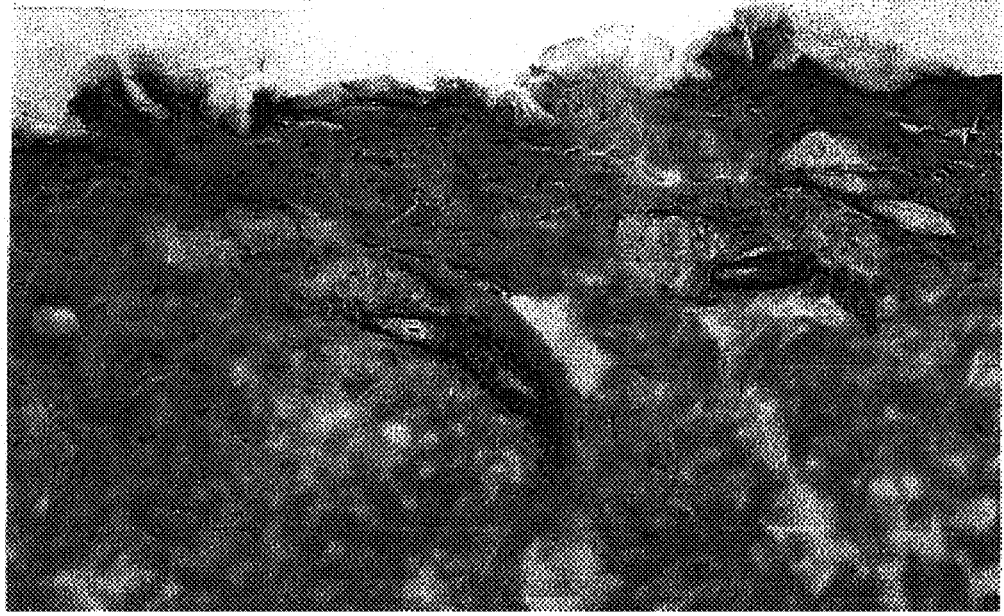

A picture of a histological sample from this Example is shown in FIG. 14. In this experiment, either 50 μl of physiological saline alone (upper "control" panel) or 350 μg of commercial PALP (having an activity of about 15 U/mg) in 50 μl of physiological saline (lower "treated" panel) was injected intradermally into shaved dorsal areas of SCID mice. Tissue samples were taken for histochemistry 48 hours after the injection. Representative sections revealed that physiological saline alone caused edema, and PALP provided complete protection against this destructive process. In addition, PALP enhanced the thickness of epidermis both on the surface of the skin and around the hair follicles (indicated by the blue color). In the PALP-treated skin (lower panel), the dermal layer was clearly healthier and more cellular than in the saline-treated skin (upper panel).

Comparative Example 17

Intradermal Injection of $\alpha_1$-Antitrypsin does not Induce Changes in the Structure of Mouse Skin Only commercial PALP was used for the above in vivo experiments. Since in in vitro experiments administration of homogeneous PALP also increased the proliferation of both keratinocytes and fibroblasts, it is highly probable that the observed changes in mouse and human skin in vivo were induced by PALP and not by a contaminant. Nevertheless, the effect of administering $\alpha_1$-antitrypsin, the major contaminant of the commercial PALP product, was also tested.

Intradermal injection of $\alpha_1$-antitrypsin (350 µg) into the dorsal skin of mice did not induce significant alterations in the epidermis or dermis (not shown). Thus, $\alpha_1$-antitrypsin did not mediate the effects observed when a PALP-containing composition was administered in the mouse skin in vivo.

Example 18

Effect of Intradermally Delivered PALP on the Structure of Human Skin

Figure 15:
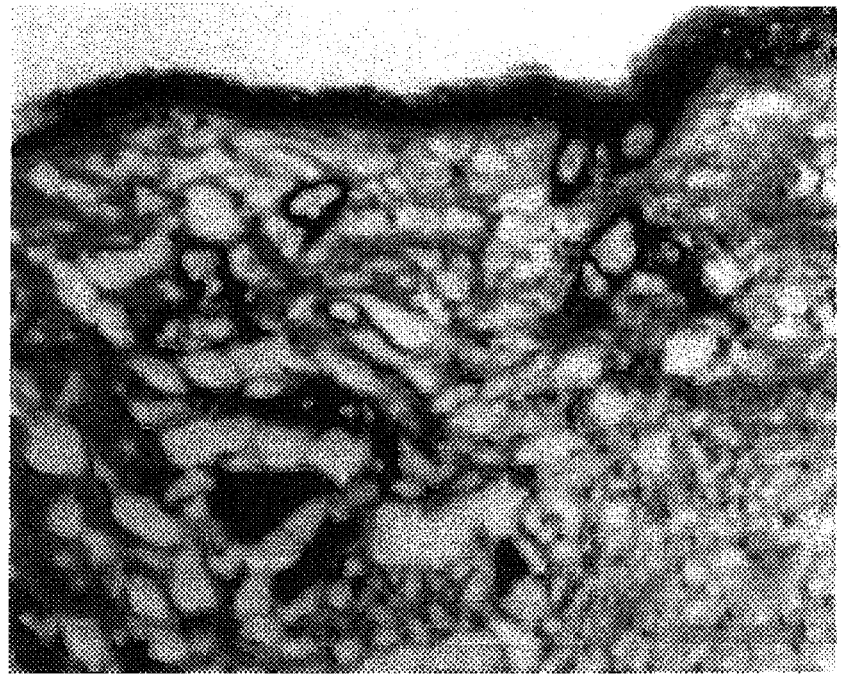
FIG. 15 (color) is a picture of a histological sample demonstrating that in human skin transplanted onto mouse back, intradermally administered PALP induces thickening of the epidermal layer and prevents edema induced by a physiological saline (control) solution.
Figure 15:

A picture of a histological sample from this Example is shown in FIG. 15. In this experiment, either 50 µl of physiological saline alone (upper "control" panel) or 350 µg of commercial PALP (having an activity of about 15 U/mg) in 50 µl of physiological saline (lower "treated" panel) was injected intradermally into the center of a bed of human skin transplanted onto the dorsal skin of SCID mice as described above. Tissue samples were taken for histochemistry 48 hours after the injection. Representative sections revealed that physiological saline alone caused edema in the human skin, against which PALP provided significant protection. Furthermore, PALP strongly enhanced the thickness of the epidermis, although in this case the increase in thickness was uneven and resulted in the formation of finger-like projections of epidermis. The exact reason for this pattern of epidermal growth in human skin is presently unknown.

In the PALP-treated human skin (lower panel), the dermal layer was again clearly healthier and more cellular than in the vehicle-treated skin (upper panel).

Comparison of data obtained with mouse and human skin indicates that both types of skin respond to PALP by increasing the thickness of epidermis and the number of dermal cells. In addition, in both cases PALP also enhanced the growth of epidermal layer in the hair follicles, suggesting that PALP may promote hair growth in human skin as well.

Example 19

Detection of Proliferating Epidermal Cells and Fibroblasts by Labeling with Bromodeoxyuridine BrdU A different set of experiments with SCID mice having human skin transplanted onto the dorsal skin was performed to detect proliferation of epidermal and dermal cells. Two control mice injected intradermally with physiological saline, and two mice injected intradermally with the PALP/saline solution, were subsequently injected intraperitoneally with 5 mg of bromodeoxyuridine ("BrdU," commercially available from Sigma-Aldrich, Inc.), and sacrificed 2 hours after that injection. Skin tissue blocks were fixed overnight in 95% ethanol/1% acetic acid and then embedded in paraffin. Sections (6 µm) were treated with a peroxidase-conjugated monoclonal antibody directed against BrdU (available from Sigma-Aldrich, Inc.), stained with the diaminobenzidine peroxidase substrate kit (Vector Laboratories, Burlingame, Calif.) and counterstained with hematoxylin. Ten sections of uniform size were analyzed for stained cells in the epidermis and dermis for both the untreated and PALP-treated animals.

For PALP-treated subjects, the human epidermal and dermal layers contained, respectively, about 6.1-times and 3.5-times more cells labeled with BrdU than the corresponding sections derived from control animals. The number of BrdU-labeled cells in untreated epidermis ranged between 0 and 6, and the number of BrdU-labeled cells in PALP-treated epidermis ranged between 8 and 19. The number of BrdU-labeled cells in untreated dermis ranged between 1 and 8, and the number of BrdU-labeled cells in PALP-treated epidermis ranged between 7 and 24. This is a further indication that PALP treatment induced proliferation of corresponding cell types in both skin layers.

The relatively low proliferation rate in the control human skin indicates that while the transplanted skin survives in the host, neither the epidermal nor the dermal layer may be able to undergo the normal renewal process (i.e. replacement of dead cells). Because PALP clearly has a positive effect on human skin, it is envisioned that administration of PALP can also enhance the viability of human skin before, during, and after transplantation into a host.

What is claimed is:

1. A method for stimulating proliferation of cells in an epidermis and a dermis of undamaged mammalian skin, comprising the step of topically administering to an area of the skin a composition comprising *Vaselinum flavum, Vaselinum album* or *Vaselinum cholesterinatum*, and human placental alkaline phosphatase.

2. The method of claim 1, wherein the skin is human skin.

3. The method of claim 1, wherein the composition is administered in an effective amount to enhance proliferation of keratinocytes in the epidermis.

4. The method of claim 1, wherein the composition is administered in an effective amount to enhance proliferation of fibroblasts in the dermis.

5. The method of claim 1, wherein the composition is administered in an effective amount to enhance both proliferation of fibroblasts in the dermis and proliferation of keratinocytes in the epidermis.

6. The method of claim 1, wherein the composition is in the form of a gel, a cream, a lotion, an unguent, an emollient, a colloidal dispersion, a suspension, an emulsion, an oil, a spray, a foam, or a mousse.

7. The method of claim 1, wherein the composition is in the form of a gel.

8. The method of claim 1, wherein the composition further includes an additive that enhances penetration of the human placental alkaline phosphatase into the skin.

9. The method of claim 1, wherein the composition essentially contains *Vaselinum cholesterinatum* as a carrier, and human placental alkaline phosphatase dispersed in the carrier.

10. The method of claim 1, wherein the composition comprises about 0.01 to about 1 wt.-% human placental alkaline phosphatase.

11. The method of claim 1, wherein the composition comprises about 0.1 to about 0.5 wt.-% human placental alkaline phosphatase.

12. The method of claim 1, wherein the composition includes homogeneous human placental alkaline phosphatase.

13. The method of claim 1, wherein the composition includes extracted human placental alkaline phosphatase.

14. The method of claim 1, wherein the composition includes synthetic human placental alkaline phosphatase.

15. The method of claim 1, wherein the composition includes recombinant human placental alkaline phosphatase.

16. A method for restoring or maintaining strength and thickness of aging skin, comprising periodically administering by topical application to the skin a composition comprising *Vaselinum flavum* or *Vaselinum album*, and an amount of human placental alkaline phosphatase.

17. The regimen of claim 16, wherein the step of periodic administration includes applying the composition once per day.

18. The regimen of claim 16, wherein the step of periodic administration includes applying the composition about once per week.

19. The regimen of claim 16, wherein the step of periodic administration includes applying the composition:
- about once per day, during a first week;
- about three times during a second week following the first week;
- about two times during a third week; and
- about once per week thereafter.

20. A method for stimulating proliferation of cells in an epidermis and a dermis of transplanted skin, comprising the step of topically administering to an area of the transplanted skin a composition comprising *Vaselinum flavum* or *Vaselinum album*, and human placental alkaline phosphatase.

21. The method of claim 20, wherein the transplanted skin is human skin.

22. The method of claim 20, wherein the transplanted skin has been transplanted onto a human host.

23. The method of claim 20, and further comprising the step of topically administering the composition to an area of host skin that is adjacent to the transplanted skin.

24. A composition for topical application comprising *Vaselinum flavum, Vaselinum album* or Vaselinum cholesterinatum, and an amount of human placental alkaline phosphatase effective to stimulate proliferation of cells in an epidermis and a dermis of mammalian skin.

25. The composition of claim 24, wherein the composition further includes an additive that enhances penetration of the human placental alkaline phosphatase into the skin.

26. The composition of claim 24, wherein the composition essentially contains *Vaselinum flavum* and human placental alkaline phosphatase.

27. The composition of claim 24, wherein the composition essentially contains *Vaselinum album* and human placental alkaline phosphatase.

28. The composition of claim 24, wherein the composition essentially contains *Vaselinum cholesterinatum* and human placental alkaline phosphatase.

29. The composition of claim 24, wherein the composition contains about 0.1 to about 1 wt.-% human placental alkaline phosphatase.

* * * * *